(12) United States Patent
Melnyk et al.

(10) Patent No.: US 9,671,397 B2
(45) Date of Patent: Jun. 6, 2017

(54) METHOD FOR FUNCTIONALIZING SURFACES FOR ANALYTE DETECTION

(75) Inventors: Oleg Melnyk, Annoeullin (FR); Jean-Philippe Georges Bernard Ebran, Lille (FR); Julien Philippe Dheur, La Bassee (FR); Nabil Dendane, Paris (FR); Vianney Souplet, Maing (FR); Christophe Olivier, Seclin (FR)

(73) Assignees: Centre National De La Recherche Scientifique, Paris (FR); Innobiochips, Lille (FR); Universite De Lille 2 Droit Et Sante, Lille (FR); Universite De Lille 1 Sciences Et Technologies, Villeneuve D'Ascq (FR)

( * ) Notice: Subject to any disclaimer, the term of this patent is extended or adjusted under 35 U.S.C. 154(b) by 983 days.

(21) Appl. No.: 13/880,263

(22) PCT Filed: Oct. 11, 2011

(86) PCT No.: PCT/IB2011/054472
§ 371 (c)(1),
(2), (4) Date: Apr. 18, 2013

(87) PCT Pub. No.: WO2012/052874
PCT Pub. Date: Apr. 26, 2012

(65) Prior Publication Data
US 2013/0203629 A1 Aug. 8, 2013

(30) Foreign Application Priority Data

Oct. 18, 2010 (FR) ...................................... 10 58469
Oct. 18, 2010 (FR) ...................................... 11 52558

(51) Int. Cl.
| G01N 33/543 | (2006.01) |
| C08B 37/00 | (2006.01) |
| C08B 37/02 | (2006.01) |
| G01N 33/548 | (2006.01) |
| C09D 105/02 | (2006.01) |

(52) U.S. Cl.
CPC ... *G01N 33/54353* (2013.01); *C08B 37/0021* (2013.01); *C09D 105/02* (2013.01); *G01N 33/548* (2013.01); *G01N 33/54393* (2013.01); *G01N 2400/22* (2013.01)

(58) Field of Classification Search
None
See application file for complete search history.

(56) References Cited

U.S. PATENT DOCUMENTS

| 4,740,594 | A | 4/1988 | Mauzac et al. |
| 5,773,227 | A | 6/1998 | Kuhn et al. |
| 6,646,120 | B1 | 11/2003 | Chaubet et al. |
| 6,946,443 | B2 | 9/2005 | Blanchat et al. |
| 7,101,863 | B2 | 9/2006 | Dahricorreia et al. |
| 8,241,620 | B2 | 8/2012 | Dahri-Correia et al. |
| 2003/0171333 | A1 | 9/2003 | Avramoglou et al. |
| 2009/0116020 | A1 | 5/2009 | Wu et al. |

FOREIGN PATENT DOCUMENTS

| EP | 0 146 455 A2 | 6/1985 |
| EP | 1 953 555 A1 | 8/2008 |
| EP | 2 030 677 A2 | 3/2009 |
| FR | 2 794 649 A1 | 12/2000 |
| FR | 2 891 149 A1 | 3/2007 |
| WO | WO 87/03372 A1 | 6/1987 |
| WO | WO-95/24429 A1 | 9/1995 |
| WO | WO-99/29734 A1 | 6/1999 |
| WO | WO 00/05316 A1 | 2/2000 |
| WO | WO-00/48576 A1 | 8/2000 |
| WO | WO-00/76452 A2 | 12/2000 |
| WO | WO-00/76562 A1 | 12/2000 |
| WO | WO-01/91742 A1 | 12/2001 |
| WO | WO-2005/095507 A1 | 10/2005 |
| WO | WO 2007/049269 A1 | 5/2007 |
| WO | WO-2007/058654 A1 | 5/2007 |

OTHER PUBLICATIONS

Carion, et al.; "*Chemical Micropatterning of Polycarbonate for Site-Specific Peptide Immobilization and Biomolecular Interactions*;" ChemBioChem, vol. 8, No. 3; pp. 315-322; <http://onlinelibrary.wiley.com/doi/10.1002/cbic.200600504/abstract>.
Gehring, et al.; Analytical and Bioanalytical Chemistry; dated Apr. 5, 2008.
Graves, H. C. B.; "*The effect of surface charge on non-specific binding of rabbit immunoglobulin G in solid-phase immunoassays*;" Journal of Immunological Methods, vol. 111, No. 2; pp. 157-166; dated Jul. 22, 1988; abstract retrieved on Jul. 29, 2013 from <http://www.sciencedirect.com/science/article/pii/0022175988901238>.
Leinonen, M., et al.; "*Class-Specific Antibody Response to Group B Neisseria meningitidis Capsular Polysaccharide: Use of Polylysine Precoating in an Enzyme-Linked Immunosorbent Assay*;" Infection and Immunity, vol. 38, No. 3; pp. 1203-1207; dated Dec. 1982; retrieved on Jul. 29, 2013 from <http://iai.asm.org/content/38/3/1203.full.pdf+html>.
Marson, A., et al.; "*Development of a microtiter plate-based glycosaminoglycan array for the investigation of glycosaminoglycan-protein interactions*;" Glycobiology, vol. 19, No. 12; pp. 1537-1546; dated Sep. 3, 2009; retrieved on Jul. 29, 2013 from <http://glycob.oxfordjournals.org/content/19/12/1537.full.pdf+html>.
Olivier, C., et al.; "*αOxo Semicarbazone Peptide or Oligodeoxynucleotide Microarrays*;" Bioconjugate Chemistry, vol. 14, No. 2; pp. 430-439; dated Mar. 2003; abstract retrieved on Jul. 29, 2013 from <http://pubs.acs.org/doi/abs/10.1021/bc025571q>.
International Search Report and Written Opinion for Application No. PCT/IB2011/054472; dated Feb. 14, 2012.
Preliminary Search Report and Written Opinion for French Application No. FA746483; dated May 26, 2011.
Preliminary Search Report and Written Opinion for French Application No. FA749295; dated Aug. 22, 2011.

*Primary Examiner* — Kaijiang Zhang
(74) *Attorney, Agent, or Firm* — Alston & Bird LLP

(57) ABSTRACT

The invention relates to a device for detecting analytes, including a plastic substrate at least partially covered by bonding polymers attached to the substrate in a non-covalent manner, said bonding polymers comprising a polysaccharide backbone provided with aromatic groupings and carboxylic acid groupings.

14 Claims, 6 Drawing Sheets

SEQUENCE LISTING

```
<160> NUMBER OF SEQ ID NOS: 9

<210> SEQ ID NO 1
<211> LENGTH: 2
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (1)..(1)
<223> OTHER INFORMATION: Rhodamine group at the N-terminal end
<220> FEATURE:
<221> NAME/KEY: MISC_FEATURE
<222> LOCATION: (2)..(2)
<223> OTHER INFORMATION: NH(CH2)3-NH-CHOCO

<400> SEQUENCE: 1

Lys Arg
1

<210> SEQ ID NO 2
<211> LENGTH: 2
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (1)..(1)
<223> OTHER INFORMATION: Rhodamine group at the N-terminal end
<220> FEATURE:
<221> NAME/KEY: MISC_FEATURE
<222> LOCATION: (2)..(2)
<223> OTHER INFORMATION: NH2 group at the C-terminal end

<400> SEQUENCE: 2

Lys Arg
```

-continued

```
<210> SEQ ID NO 3
<211> LENGTH: 32
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (32)..(32)
<223> OTHER INFORMATION: NH2 group at the C-terminal end

<400> SEQUENCE: 3

Ser Gly Tyr Pro Tyr Asp Val Pro Asp Tyr Ala Gly Tyr Pro Tyr Asp
1               5                   10                  15

Val Pro Asp Tyr Ala Gly Tyr Pro Tyr Asp Val Pro Asp Tyr Ala Ser
            20                  25                  30

<210> SEQ ID NO 4
<211> LENGTH: 26
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (26)..(26)
<223> OTHER INFORMATION: NH2 group at the C-terminal end

<400> SEQUENCE: 4

Ser Asp Tyr Lys Asp His Asp Gly Asp Tyr Lys Asp His Asp Ile Asp
1               5                   10                  15

Tyr Lys Asp Asp Asp Asp Lys Gly Gly Ser
            20                  25

<210> SEQ ID NO 5
<211> LENGTH: 31
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (1)..(1)
<223> OTHER INFORMATION: CHOCO group at the N terminal end
<220> FEATURE:
<221> NAME/KEY: MISC_FEATURE
<222> LOCATION: (31)..(31)
<223> OTHER INFORMATION: NH2 group at the C-terminal end

<400> SEQUENCE: 5

Gly Tyr Pro Tyr Asp Val Pro Asp Tyr Ala Gly Tyr Pro Tyr Asp Val
1               5                   10                  15

Pro Asp Tyr Ala Gly Tyr Pro Tyr Asp Val Pro Asp Tyr Ala Ser
            20                  25                  30

<210> SEQ ID NO 6
<211> LENGTH: 25
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (1)..(1)
<223> OTHER INFORMATION: CHOCO group at the N terminal end
<220> FEATURE:
<221> NAME/KEY: MISC_FEATURE
```

```
<222> LOCATION: (25)..(25)
<223> OTHER INFORMATION: NH2 group at the C-terminal end

<400> SEQUENCE: 6

Asp Tyr Lys Asp His Asp Gly Asp Tyr Lys Asp His Asp Ile Asp Tyr
1               5                   10                  15

Lys Asp Asp Asp Asp Lys Gly Gly Ser
            20                  25

<210> SEQ ID NO 7
<211> LENGTH: 10
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (4)..(4)
<223> OTHER INFORMATION: Rhodamine
<220> FEATURE:
<221> NAME/KEY: MISC_FEATURE
<222> LOCATION: (10)..(10)
<223> OTHER INFORMATION: NH2 group at the C-terminal end

<400> SEQUENCE: 7

Cys Ile Leu Lys Glu Pro Val His Gly Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (4)..(4)
<223> OTHER INFORMATION: Rhodamine
<220> FEATURE:
<221> NAME/KEY: MISC_FEATURE
<222> LOCATION: (10)..(10)
<223> OTHER INFORMATION: NH2 group at the C-terminal end

<400> SEQUENCE: 8

Ser Ile Leu Lys Glu Pro Val His Gly Val
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (3)..(3)
<223> OTHER INFORMATION: Mtt
<220> FEATURE:
<221> NAME/KEY: MISC_FEATURE
<222> LOCATION: (4)..(4)
<223> OTHER INFORMATION: TBu
<220> FEATURE:
<221> NAME/KEY: MISC_FEATURE
<222> LOCATION: (7)..(7)
<223> OTHER INFORMATION: Trt
<220> FEATURE:
```

```
<221> NAME/KEY: MISC_FEATURE
<222> LOCATION: (9)..(9)
<223> OTHER INFORMATION: NH2 group at the C terminal end

<400> SEQUENCE: 9

Ile Leu Lys Glu Pro Val His Gly Val
1               5
```

METHOD FOR FUNCTIONALIZING SURFACES FOR ANALYTE DETECTION

FIELD OF THE INVENTION

The present invention relates to a method of functionalizing surfaces for analyte detection. This method of functionalizing surfaces in particular gives devices for detecting analytes that can be used for implementing various chemical, biological and diagnostic assays. The invention also supplies special polymers that are suitable for applying said method of functionalizing surfaces.

TECHNICAL BACKGROUND

The reference assay in diagnostics is the so-called "ELISA" assay. With this assay it is possible to detect or determine an analyte in a biological fluid. In general, the wells of a microtitre plate are coated (by essentially hydrophobic interaction) with a capturing element (for example an antibody) capable of binding specifically to an analyte (in particular an antigen) that is being sought. The test solution is then deposited in the wells of the microplate, and if the molecule sought is present, it binds specifically to the capturing element.

A tracer element, also capable of binding to the molecule being sought, is added to the wells. This tracer element can be for example an enzyme that catalyses the formation of a coloured product, so that this tracer element can be quantified by colorimetry.

The ELISA assay is well suited to automation. However, the surfaces conventionally used for this assay (of polystyrene) cannot easily immobilize hydrophilic molecules, such as negatively charged polysaccharides, or those of low molecular weight. It has also been proposed for example to conjugate a polysaccharide with a polylysine so as to be able to fix it to a polystyrene surface, utilizing the adsorption capabilities of polylysine (Leinonen & Frasch, Infect Immun., 38(3): 1203-7, 1982).

The ELISA assay also has limitations connected with the surface charge, because the interactions are generally more specific with negatively-charged surfaces (Graves, J. Immunol. Methods, 111(2): 157-66, 1988), whereas the surfaces of plastics are hydrophobic.

Moreover, the standard ELISA assay is limited to monoparametric analyses, which means that a single piece of information is available per test and per sample. When several analyses are required on the same sample, it is necessary to carry out several assays of the ELISA type, preferably in parallel, either conventionally, or miniaturized, in a device known as a "biochip". Very few biochips are currently marketed, and the devices currently on offer mainly use glass microscope slides as substrates. Such a substrate is poorly suited to mass use.

On the other hand, plastic substrates are poorly suited to fabrication of biochips. Unsatisfactory signal/noise ratios are generally obtained in direct adsorption on the substrate, owing to the considerable nonspecific adsorption of the analytes. Hydrophobic plastic surfaces also have the drawback that they denature proteins, and therefore cannot be used without modification.

However, the possibilities of functionalization of plastics by chemical modification of the polymers in question are very limited, as few chemical groups can be introduced. Moreover, a minor change in the composition of the polymers, or even variations in composition from one batch to the next, would lead to differences in properties of the functionalized substrates.

Moreover, important constraints are encountered during printing of biochips, as it is difficult to deposit nanodrops reproducibly (so as to obtain deposits that are well defined and regular) on such substrates. The most practical method for depositing drops in this context, contact printing with needles, is a technical challenge, so that the contactless deposition technique of the piezoelectric type is generally used. However, in view of its slowness, the latter is not very suitable for industrial production.

Some examples of functionalization of 96-well plastic plates have been proposed. Thus, the plasma technique was suggested in Marson, Robinson et al., Glycobiology 19(2): 1537-46 (2009), for preparing sugar-based chips. This technique poses the difficulty of preserving the functionality of the sugar after immobilization. Another example is based on the use of streptavidin for coating plastic surfaces (Gehring, Albin et al., Anal. Bioanal. Chem., 5 Apr. 2008).

Document EP 1 953 555 describes a device comprising a plastic substrate covered with a metallic film on which a physiologically active substance and a compound for creating hydrogen bonds are immobilized.

Document EP 2 030 677 describes a biosensor comprising a substrate covered with a metallic film, by means of which an anionic polymer is fixed.

These documents do not disclose a direct interaction between the polymer and a plastic substrate.

There is therefore still a need to supply devices for detecting analytes that are easy to manufacture, robust, easy to use, and/or that make it possible to detect a large number of analytes in parallel.

SUMMARY OF THE INVENTION

The invention relates firstly to a device for detecting analytes, comprising a plastic substrate covered at least partly with bonding polymers fixed to the substrate non-covalently, said bonding polymers comprising a polysaccharide skeleton provided with aromatic groups and carboxylic acid groups.

According to an embodiment, the polysaccharide skeleton is a dextran skeleton, the molecular weight of which is preferably between 15 000 and 100 000, and more particularly preferably between 30 000 and 60 000.

According to an embodiment, the polysaccharide skeleton is further provided with reactive groups, said reactive groups preferably being of the form —X—CONH—Z', where X represents a linear or branched, substituted or unsubstituted alkyl chain, comprising 1 to 6 carbon atoms, X being more particularly preferably $CH_2$, and Z' represents a group that is able to bind to another molecule.

According to an embodiment, the carboxylic acid groups are of the form —X—COOH, where X represents a linear or branched, substituted or unsubstituted alkyl chain, comprising 1 to 6 carbon atoms, X preferably being $CH_2$.

According to an embodiment, the aromatic groups are of the form —X—CONH—Z, where X represents a linear or branched, substituted or unsubstituted alkyl chain, comprising 1 to 6 carbon atoms, X preferably being $CH_2$, and Z represents an aryl function, preferably comprising 6 to 30 carbon atoms, Z preferably being an optionally substituted benzyl function, such as —$CH_2$-Ph or —$CH_2$-Ph-paraOH.

According to an embodiment, the bonding polymers comprise:

from 0.4 to 0.8 aromatic groups, preferably from 0.4 to 0.6 aromatic groups, preferably from 0.45 to 0.6 aromatic groups per saccharide unit of the polysaccharide skeleton; and/or from 0 to 0.8 reactive groups, preferably from 0 to 0.6 reactive groups, per saccharide unit of the polysaccharide skeleton; and/or from 0.5 to 1.5 aromatic, carboxylic acid and reactive groups in total, preferably from 0.9 to 1.3 aromatic, carboxylic acid and reactive groups in total, per saccharide unit of the polysaccharide skeleton.

According to an embodiment, the substrate is a substrate of polystyrene, polycarbonate, poly(methyl methacrylate) or polypropylene, and preferably of polystyrene.

According to an embodiment, the device comprises capturing elements immobilized on the bonding polymers, said capturing elements preferably being selected from polypeptides, optionally modified and/or conjugated, saccharides, oligosaccharides or lipopolysaccharides, viruses or virus fragments and cells, the capturing elements preferably being immobilized on the bonding polymers by adsorption or by covalent bonding to the reactive F groups.

According to an embodiment, the device comprises a plurality of detection zones, the detection zones preferably comprising different capturing elements.

According to an embodiment, the substrate is an opaque or transparent slide, a microtitre plate, a collection of beads, a culture plate, a strip or a stick.

The invention also relates to a polymer comprising a polysaccharide skeleton provided with aromatic groups, carboxylic acid groups as well as reactive groups of formula (V):

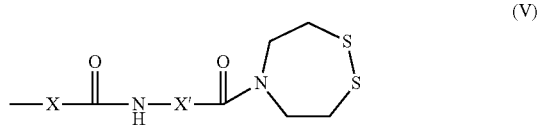

X and X' each representing a substituted or unsubstituted alkyl chain, comprising from 1 to 6 carbon atoms.

The invention also relates to a polymer comprising a polysaccharide skeleton provided with aromatic groups, carboxylic acid groups as well as reactive groups of formula (V'):

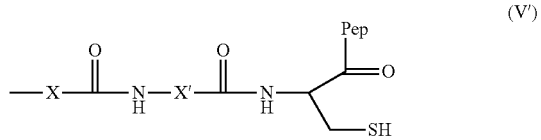

X and X' each representing a substituted or unsubstituted alkyl chain comprising from 1 to 6 carbon atoms and Pep representing a peptide fragment.

According to an embodiment of the two aforementioned polymers, X represents $CH_2$ and/or X' represents $(CH_2)_2$.

The invention also relates to a method of manufacturing the above polymer endowed with reactive groups of formula (V), comprising:

supplying a polysaccharide;
grafting carboxylic acid groups on the polysaccharide; then
modifying a proportion of the grafted carboxylic acid groups to supply aromatic groups; followed or preceded by
modifying another proportion of the grafted carboxylic acid groups to supply reactive groups of formula (V), said modification comprising reaction of the polysaccharide with the compound of formula (VII):

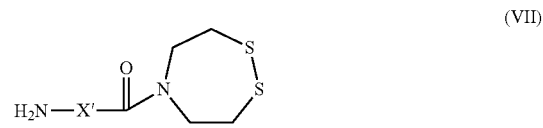

in which X' represents a substituted or unsubstituted alkyl chain, comprising from 1 to 6 carbon atoms.

The invention also relates to a method of manufacturing the above polymer endowed with reactive groups of formula (V'), comprising:

supplying a polymer of formula (V) above; and
reacting this polymer with the polypeptide H-Cys-Pep, where Pep represents a peptide fragment and Cys represents the cysteine residue.

According to an embodiment of the device described above, the bonding polymers are aforementioned polymers (endowed with reactive groups of formula (V) or (V')).

The invention also relates to the use of a device for detecting analytes as described above, for detecting and optionally quantifying chemical molecules, biological molecules, cells or living organisms.

The invention also relates to a method of manufacturing a device for detecting analytes as described above, comprising:

supplying a plastic substrate;
contacting the substrate with at least one solution comprising bonding polymers.

According to an embodiment, this method further comprises contacting the substrate with one or more solutions comprising capturing elements.

The invention also relates to a method of manufacturing a device for detecting analytes as described above, comprising:

supplying a plastic substrate;
contacting the substrate with one or more solutions comprising bonding polymers bound to capturing elements.

The present invention makes it possible to overcome the drawbacks of the prior art. More particularly it provides devices for detecting analytes that are easy to manufacture, robust and easy to use. According to an embodiment, these devices make it possible to detect a large number of analytes in parallel. In particular, the invention makes it possible to immobilize hydrophilic and/or small molecules (but also antibodies or proteins).

This is achieved through surface functionalization by means of bonding polymers having a polysaccharide skeleton. The bonding polymers comprise aromatic groups, which promote non-covalent fixation of the bonding polymers to relatively hydrophobic surfaces, as well as carboxylic acid groups, for negatively charging the bonding polymers so as to limit the phenomena of nonspecific adsorption between the bonding polymers and the analytes to be detected (which are themselves often negatively charged).

The use of plastic and in particular polystyrene surfaces in the devices of the invention makes it possible to avoid the problems associated with glass: risk of breakage of glass and associated danger for the personnel, costs connected with waste disposal, heterogeneity of functionalization associated with the chemical nature of glass, high cost of the substrate and of characterization, difficulty of partitioning the substrate.

According to certain particular embodiments, the invention also has one or preferably several of the advantageous features enumerated below.

The bonding polymers are easily synthesized in large quantities and can be characterized by conventional analytical techniques (NMR, pH measurement, microanalysis), allowing rigorous control of manufacture.

The bonding polymers are fixed on the surfaces by simple adsorption (non-covalent bonding), in particular by means of the aromatic groups of the bonding polymers. This is a manner of fixation that is particularly simple to implement, robust, and is not very sensitive to moderate variations of the physicochemical properties of the surfaces. It is in any case also possible to adjust the density of the aromatic groups in the bonding polymers, in relation to the nature of the surfaces.

The invention can be implemented starting from substrates that are currently widely available and inexpensive: microtitre plates made of polystyrene, Petri dishes etc.

The invention can also be used for making biochips, i.e. miniaturized devices for detecting analytes for parallel detection of a large number of analytes, based on plastic and in particular polystyrene substrates.

The surface functionalization according to the invention is carried out by fixing capturing elements (or probes) on the bonding polymers, either covalently (via reactive groups present on the bonding polymers), in particular when the capturing elements are small molecules, or else non-covalently (by adsorption). Thus, the invention offers great flexibility of application.

The functional groups are advantageously stable (conserving their properties) in the presence of moisture or air.

DESCRIPTION OF EMBODIMENTS OF THE INVENTION

Figure 1:
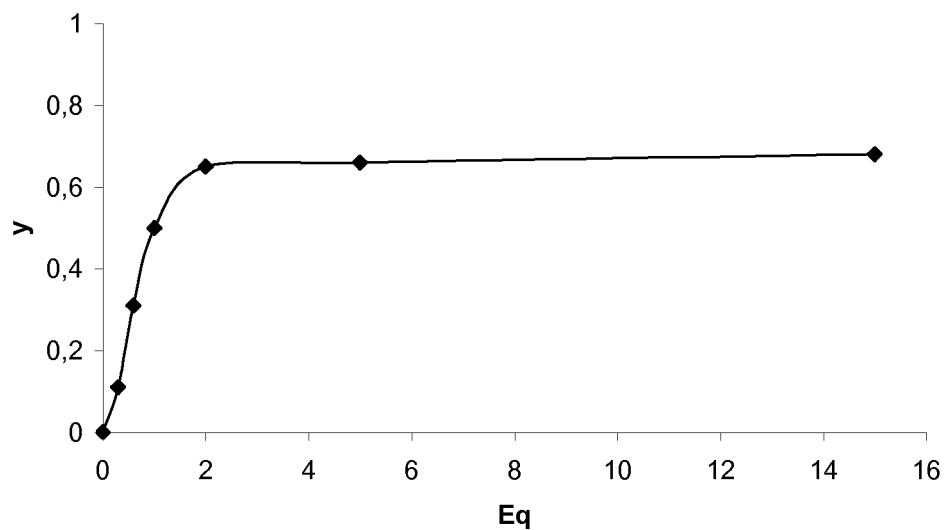
FIG. 1 shows the relationship between the degree of substitution with aromatic groups (on the y axis) in the polymer PsAcAr1 from Example 3, relative to the number of benzylamine equivalents (on the x axis). This will be referred to in Example 4.

The invention is now described in more detail and non-limitatively in the following description.

Bonding Polymers and Manufacture Thereof

The bonding polymers used in the context of the invention comprise a polysaccharide skeleton (abbreviation "Ps" hereinafter) provided with carboxylic acid groups (abbreviation "Ac" hereinafter) and aromatic groups (abbreviation "Ar" hereinafter). According to an embodiment, the polysaccharide skeleton can also be provided with reactive groups different from the aforementioned carboxylic acid groups (abbreviation "F" hereinafter).

By "polysaccharide skeleton" is meant a structure formed by an assemblage of sugars (or saccharide units), joined together by O-osidic bonds. This structure can be linear or branched. It preferably comprises from 80 to 600 saccharide units, and more particularly preferably from 150 to 350 saccharide units.

The saccharide units are preferably cyclic. They can be trioses, tetraoses, pentoses, hexoses or heptoses, and preferably they are hexoses.

"Level of substitution" or "degree of substitution" is the average number of substituents (Ac, Ar or F) per saccharide unit. Methods of determining the degrees of substitution are given in the examples section.

All of the Ac, Ar and F groups are preferably grafted on some or all of the hydroxyl functions of the saccharide units.

The molecular weight of the polysaccharide skeleton is preferably comprised between 15 000 and 100 000, and more particularly preferably between 30 000 and 60 000.

The polysaccharide skeleton can be of the homopolysaccharide type (identical saccharide units) or heteropolysaccharide type (different saccharide units).

As examples of homopolysaccharides, there may be mentioned: the glucosans or glucans (alpha-glucans or beta-glucans), such as starch, glycogen, cellulose, dextran, pullulan, hyaluronic acid, chitin or chitosan (deacetylated forms of chitin); arabinans, xylans and pectins. As examples of heteropolysaccharides, there may be mentioned gums, which are branched structures comprising D-galactose, L-arabinose, L-rhamnose, and D-glucuronic acid, as well as the hemicelluloses.

According to a preferred embodiment, the saccharide units are glucose (or dextrose) units. Preferably, the polysaccharide skeleton is a dextran molecule, i.e. it has a main chain of glucoses joined together by α-1,6 glycosidic bonds optionally with branchings attached to the main chain by α-1,2 and/or α-1,3 and/or α-1,4 bonds. Dextran is available in large quantities, is inexpensive and has good solubility in water.

In the rest of the description, reference will be made to a polysaccharide skeleton of the dextran type, it being understood that this description applies analogously to other types of polysaccharide skeletons.

The bonding polymers according to the invention that are not provided with reactive F groups (polymers of the "PsAcAr" type) can be obtained by:
supplying a polysaccharide Ps (unsubstituted polysaccharide skeleton);
grafting Ac groups on this polysaccharide so as to obtain a polymer of the "PsAc" type;
modifying a proportion of the Ac groups of the polymer PsAc to obtain the polymer PsAcAr.

Thus, referring to general formula (I) below:

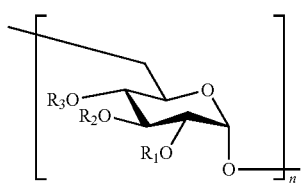

the starting polymer Ps is a polymer of formula (I) in which all the $R_1$, $R_2$ and $R_3$ groups represent a hydrogen atom; the intermediate polymer PsAc is a polymer of formula (I) in which some $R_1$, $R_2$ and $R_3$ groups represent a hydrogen atom and the other $R_1$, $R_2$ and $R_3$ groups represent a group bearing a carboxylic acid function; and the bonding polymer PsAcAr is a polymer of formula (I) in which some $R_1$, $R_2$ and $R_3$ groups represent a hydrogen atom, other $R_1$, $R_2$ and $R_3$ groups represent a group bearing a carboxylic acid function and the third and last proportion of the $R_1$, $R_2$ and $R_3$ groups represent a group bearing an aromatic nucleus.

The carboxylic acid Ac groups are of the form —X—COOH, where X represents a linear or branched alkyl chain comprising 1 to 6 carbon atoms, optionally provided with one or more substituents selected from chlorine, bromine, a ketone group, fluorine, an alcohol group, a carboxylic acid group and an aromatic group (in particular phenyl). Preferably, this chain is linear and unsubstituted and/or comprises at most 5 carbon atoms, at most 4 carbon atoms, at most 3 carbon atoms or at most 2 carbon atoms. According to a preferred embodiment, in which possible problems of excessive reactivity are avoided, the Ac groups are of the form —CH$_2$—COOH (methylcarboxylic acid groups).

It is understood that the Ac groups can be in the ionized form (COOH replaced with COO⁻ associated with a counter-ion) or in the salified form (COOH replaced for example with COONa) depending on the context.

Preferably the Ac groups are all identical, but it is also possible to envisage grafting of different Ac groups.

The aromatic Ar groups are of the form —Y—Z where Y represents a binding group and Z represents an aryl function, preferably comprising 6 to 30 carbon atoms, preferably from 6 to 24 carbon atoms, more particularly from 6 to 12 carbon atoms, and one or more substituents selected from the halogens, —OH, —NH$_2$, —NO$_2$, —OR', —COOR', —CONHR' where R' is an alkyl group having from 1 to 6 carbon atoms. Z can be monocyclic or polycyclic, and optionally heterocyclic. Z is preferably a benzene derivative, and in particular a phenyl, benzyl or phenol group.

Y is preferably an amide group of the form —X—CONH—, where X has the same meaning as given above in relation to the Ac groups.

According to a preferred embodiment, the Ar groups are —CH$_2$—CONH—CH$_2$-Ph groups (where Ph is a phenyl group) or —CH$_2$—CONH—CH$_2$-Ph-paraOH groups.

Preferably, the Ar groups are all identical, but it is also possible to envisage grafting of different Ar groups.

The step of grafting Ac groups on the polysaccharide Ps to obtain the polymer PsAc can be carried out by reacting the polysaccharide Ps with a carboxylic acid compound bearing a halogen function, and preferably a chlorine function.

For example, grafting of the preferred Ac groups of the form —CH$_2$—COOH can be obtained by reacting the polysaccharide Ps with monochloroacetic acid. Preferably, the reaction is carried out in the presence of isopropanol.

The step of modifying a proportion of the Ac groups of the polymer PsAc to obtain the polymer PsAcAr can be carried out by reacting the polymer PsAc with a compound of the R—Z type where Z has the same meaning as above, and R is a function that is reactive with the carboxylic function. Preferably, R is an amine function, capable of forming an amide bond with the Ac groups.

For example, the preferred Ar groups of the —CH$_2$—CONH—CH$_2$-Ph type can be obtained by reacting the polysaccharide PsAc with benzylamine. As a further example, the preferred Ar groups of the —CH$_2$—CONH—CH$_2$-Ph-paraOH type can be obtained by reacting the polysaccharide PsAc with para-hydroxybenzylamine. Preferably, the reaction is carried out in the presence of 1-cyclohexyl-3-(2-morpholinoethyl)carbodiimide.

The bonding polymers according to the invention that are provided with reactive F groups (polymers of the "PsAcArF" type) can be obtained starting from polymers of the PsAc type (such as obtained above), by modifying a proportion of the Ac groups on the one hand to F groups and on the other hand to Ar groups. These two modification steps can be carried out in any order.

In other words, first a polymer of the PsAcAr type can be produced from a polymer PsAc (as was described above), then this polymer of the PsAcAr type can be modified to obtain the polymer of the PsAcArF type. It is also possible to produce a polymer of the "PsAcF" type first from a polymer PsAc, and then modify this polymer of the PsAcF type to obtain the polymer of the PsAcArF type (the method used for this second modification being the same as that used for modifying the polymer of the PsAc type to polymer of the PsAcAr type).

The advantage of these various strategies is to allow modulation of the degrees of substitution according to whether a higher level of Ar groups, or a higher level of F group is required.

Referring to general formula (I) below:

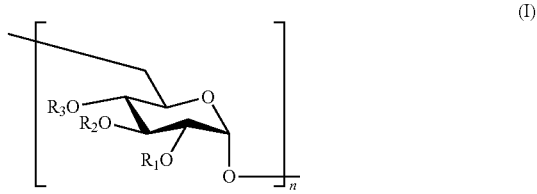

the polymer PsAcF is a polymer of formula (I) in which some $R_1$, $R_2$ and $R_3$ groups represent a hydrogen atom, other $R_1$, $R_2$ and $R_3$ groups represent a carboxylic acid group and the third and last proportion of the $R_1$, $R_2$ and $R_3$ groups represent a reactive group (different from the carboxylic acid group); and the polymer PsAcArF is a polymer of formula (I) in which some $R_1$, $R_2$ and $R_3$ groups represent a hydrogen atom, other $R_1$, $R_2$ and $R_3$ groups represent a carboxylic acid group, further $R_1$, $R_2$ and $R_3$ groups represent an aromatic group and the fourth and last proportion of the groups $R_1$, $R_2$ and $R_3$ represent a reactive group (different from the carboxylic acid group).

The reactive F groups are of the form —Y—Z', where Y represents a binding group (same meaning as above) and Z' represents a group that is able to bind, in particular covalently, to a capturing element, as described in more detail below. According to a preferred embodiment, group Z' is able to form a covalent bond with a polypeptide.

Y is preferably an amide group of the form —X—CONH—, where X has the same meaning as given above in relation to the Ac groups (and X is preferably $CH_2$).

According to a first preferred embodiment, the Z' groups are azide groups (and in particular alkylazides), and the F groups are preferably groups of the form —X—CONH—X'—$N_3$ where X and X' each represent a substituted or unsubstituted alkyl chain, comprising from 1 to 6 carbon atoms, the F groups can therefore for example be —$CH_2$—CONH—$(CH_2)_3$—$N_3$ groups. Such groups are particularly useful as intermediate groups, making it possible to obtain for example groups of the triazole type (see the third embodiment below). They can also bind to certain capturing elements.

According to a second preferred embodiment, the Z' groups are hydrazide groups, and the F groups are preferably groups of the form —X—CONH—$NH_2$ where X represents a substituted or unsubstituted alkyl chain, comprising from 1 to 6 carbon atoms, the F groups can therefore for example be —$CH_2$—CONH—$NH_2$ groups. These F groups are able to bind to an aldehyde function of peptides for example. They can also promote the adsorption of polypeptides (non-covalent immobilization).

According to a third preferred embodiment, the Z' groups are triazole groups, preferably substituted with one or more linear or branched, substituted or unsubstituted alkyl chains comprising from 1 to 6 carbon atoms, and the F groups can therefore for example be groups of formula (II):

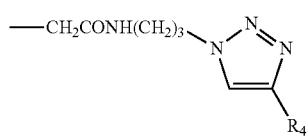

(II)

in which $R_4$ represents the group of formula (III):

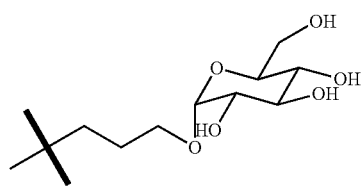

(III)

F groups of this type can bind certain particular capturing elements. The F groups of formula (II) above where $R_4$ represents —$(CH_2)_3$OH are used as negative controls in the examples.

According to a fourth preferred embodiment, the Z' groups are of the following formula (IV):

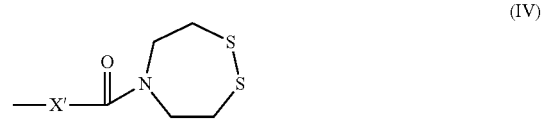

(IV)

in which X' represents a linear or branched alkyl chain comprising 1 to 6 carbon atoms, optionally provided with halogen substituents (in particular Cl or Br). Preferably X' is $(CH_2)_2$. According to this fourth embodiment, the F groups are therefore preferably of the following formula (V):

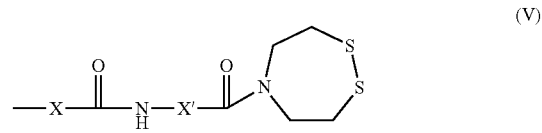

(V)

in which X and X' have the meaning given above. According to a particularly preferred embodiment, X represents $CH_2$ and X' represents $(CH_2)_2$.

The F groups corresponding to this fourth embodiment can react with the molecules bearing a beta-aminothiol or gamma-aminothiol function, for example the polypeptides having a cysteine or a homocysteine in N-terminal position, to form an amide bond. Thus, the bonding polymers corresponding to this fourth embodiment can bind to capturing elements formed by polypeptides having a cysteine or a homocysteine in N-terminal position.

Thus, in the case of a cysteine, a bonding polymer is obtained in which the F groups bound to the capturing elements are of formula (V'):

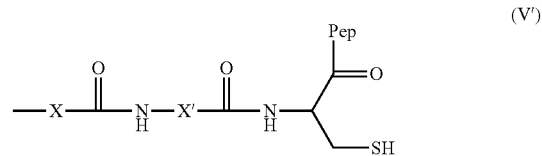

(V')

X and X' having the above meaning and Pep representing a peptide fragment, i.e. a portion of polypeptide comprising at least one amino acid residue (preferably a succession of several amino acid residues), provided with a C-terminal function (for example COOH or $CONH_2$).

The F groups can all be identical, or else grafting of different F groups can be envisaged.

The step of modifying a proportion of the Ac groups of the polymer PsAc (respectively of the polymer PsAcAr) to obtain the polymer PsAcF (respectively of the polymer PsAcArF) can be carried out by reacting the polymer PsAc (respectively of the polymer PsAcAr) with a compound of the type R—Z', where Z' has the same meaning as above, and R is a function that is reactive with the carboxylic function. Preferably, R is an amine function, capable of forming an amide bond with the Ac groups.

Certain F groups can be grafted by grafting firstly intermediate reactive F' groups, then chemically modifying the F' groups to give the F groups after a separate reaction step.

For example, the F groups of the —$CH_2$—CONH—$NH_2$ type can be obtained by reacting the polysaccharide PsAc (or the polymer PsAcAr) with hydrazine (preferably in the presence of 1-cyclohexyl-3-(2-morpholinoethyl)carbodiimide.

The F groups of the —$CH_2$—CONH—$(CH_2)_3$—$N_3$ type can be obtained by reacting the polysaccharide PsAc (or polymer PsAcAr) with 3-azidopropylammonium hydrochloride (preferably in the presence of 1-cyclohexyl-3-(2-morpholinoethyl)carbodiimide).

The F groups of formula (II) above can be obtained by reacting a polymer PsAcF (or a polymer PsAcArF) provided with reactive groups of the type —$CH_2$—CONH—$(CH_2)_3$—$N_3$ with the compound of formula (VI):

$$\equiv R_4 \qquad (VI)$$

(preferably in the presence of copper(II) ions and sodium ascorbate).

In this instance, a polymer PsAcF (or a polymer PsAcArF) is obtained in which either all the F groups are of formula (II) above, or a proportion of the F groups are of formula (II) above and a proportion of the F groups are of the —$CH_2$—CONH—$(CH_2)_3$—$N_3$ type (in the case of incomplete substitution with the compounds of formula (VI)).

The F groups of formula (V) above can be obtained by reacting the polysaccharide PsAc (or the polymer PsAcAr) with the compound of formula (VII):

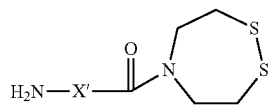

(VII)

(preferably in the presence of 1-cyclohexyl-3-(2-morpholinoethyl)carbodiimide) in which X' has the meaning given above. The compound of formula (VII) can be manufactured as indicated in the examples given below.

In general, the degree of substitution with Ac, Ar and F can be adjusted depending on the one hand on the order in which the grafting of groups is carried out (Ac then Ar then F or else Ac then F then Ar), and on the other hand by adapting the grafting conditions and in particular the molar ratio between the polysaccharide and the reagent responsible for grafting the group in question.

Polymers derived from dextrans and corresponding to the general formula of the bonding polymers given above, with sulphate or sulphonate groups for reactive F groups, as well as the use of these polymers for therapeutic purposes, have been described in documents WO 99/29734, WO 00/76452, WO 00/76562, WO 01/91742 and FR 2891149.

Preferably, the bonding polymers of the invention do not have sulphate or sulphonate functions. In fact, such functions can interact with a great many proteins, which is harmful for optimum detection. Moreover, the absence of sulphate or sulphonate functions is particularly useful when the capturing elements are themselves sulphated (oligosaccharides in particular).

Functionalization of Surfaces

The bonding polymers according to the invention (of the PsAcAr or PsAcArF type) can be deposited on a substrate in order to functionalize the surface of said substrate. The substrate is of plastic (solid material of a polymeric nature, generally shaped hot and under pressure), which is preferably selected from polystyrene, polycarbonate, poly(methyl methacrylate) and polypropylene.

Thus, the invention makes it possible for example to functionalize the surface of transparent or opaque plastic slides, or else polystyrene microtitre plates (for example 96-well), beads (magnetic or non-magnetic), polystyrene culture plates (for example 96-well), polystyrene strips or sticks.

Functionalization generally comprises two steps: a first step of fixation of the bonding polymers on the surface of the substrate and a second step of fixation of capturing elements on the bonding polymers. Alternatively, the bonding polymers can be bound to the capturing elements before fixing the bonding polymers to the surface of the substrate (especially when the bond between the bonding polymers and the capturing elements is of the covalent type).

The fixation of the bonding polymers on the surface of the substrate is carried out, in particular for flat surfaces, by immersing the surface to be treated in a solution comprising the polymer PsAcAr or PsAcArF. For moulded surfaces that can contain a liquid (for example 96-well titration plates), functionalization can be carried out by simple filling. Subsequent washing and drying is generally envisaged. In general, the polymer solution is at a concentration from 0.1 to 50 µg/mL, and preferably from 1 to 10 µg/m L.

Without wishing to be bound to any theory, the inventors think that the bonding polymers are fixed non-covalently on the surface of the substrate (adsorption) in particular via the Ar groups.

The capturing elements fixed on the bonding polymers can be polypeptides, optionally modified and/or conjugated, saccharides, oligosaccharides or lipopolysaccharides, viruses or virus fragments or even cells. For example, the capturing elements can be antibodies.

The term "polypeptide", in the context of the present application, covers any chain of amino acid residues (with a number greater than or equal to two) attached by peptide bonds. The "polypeptides" within the meaning of the present application can therefore for example be oligopeptides, peptides or proteins according to the conventional acceptation of these terms. The amino acid residues present in the polypeptides according to the invention can be selected from the proteinogenic or non-proteinogenic amino acid residues. Preferably, they are selected from the twenty proteinogenic amino acid residues.

Fixation of the capturing elements to the bonding polymers can take place by adsorption if bonding polymers without reactive F groups are used. It can also take place by establishment of covalent bonds with the reactive F groups. It can also take place by adsorption promoted by reactive F groups. This is the case for example for the adsorption of antibodies promoted by groups of the hydrazide type.

It is also possible to envisage capturing elements comprising several parts. For example, it is possible to use an intermediate capturing element (for example a polypeptide or a saccharide compound or a glycopeptide) that can fix to the bonding polymers, and a final capturing element (for example a virus or a virus fragment or a cell) that can bind to the intermediate capturing element.

When the device for analyte detection is intended only for detecting one analyte (or analytes of one type), it is sufficient to deposit the bonding polymers (and the capturing element or elements) on the whole useful surface of the substrate.

When the device for analyte detection is intended for detecting several analytes with separate capturing elements, several separate detection zones must be provided. 96-well microtitre plates are an example of a substrate that is particularly useful for this purpose.

In this case, either the bonding polymers can be deposited on the whole useful surface of the substrate, and then the various capturing elements can be deposited on delimited zones of the substrate (for example by depositing small droplets of various solutions containing the capturing elements on defined locations of the substrate); or various solutions of bonding polymers bound to the capturing elements can be deposited directly on delimited zones of the substrate (for example in the wells of a microtitre plate); or one or more solutions of bonding polymers can be deposited directly on delimited zones of the substrate (for example in the wells of a microtitre plate) and then various solutions containing the capturing elements can be deposited on the same delimited zones of the substrate.

The zones of the surface of the substrate covered with bonding polymers are preferably hydrophilic, characterized by a contact angle of water less than or equal to 70°, preferably less than or equal to 65° and ideally less than or equal to 60°. The hydrophilicity of the surface of the substrate covered with bonding polymers makes it possible to minimize the nonspecific interactions of a great many analytes (in particular proteins) with the substrate. It also makes it possible to deposit nanodrops for preparing biochips, whereas this type of deposition is complex and poorly reproducible when it is carried out directly on untreated plastic substrates.

The analytes that can be detected using the invention can be all kinds of chemical or biological materials: mineral particles, organic molecules (in particular pesticides or other pollutants), biomolecules (in particular saccharide compounds, polypeptides, modified or unmodified, conjugated or unconjugated), virus or virus fragments, cells or organisms (unicellular or multicellular).

In particular, the invention makes it possible to manufacture chips with polypeptides, useful for serotyping, screening of epitopes, quantification of proteins in biological media, or else analysis of ratios between peptide molecules of the ligand-receptor type.

In general, use of the detection devices according to the invention involves contacting the substrate surface, coated with the bonding polymers and the capturing elements, with one or more solutions or suspensions that may comprise the analytes of interest (for example sample of water from the environment, sample of foodstuff, biological sample such as urine, blood or a blood derivative product, etc.).

Detection of the analytes that are possibly fixed specifically to the capturing elements can be carried out by means of tracer elements, which can be for example fluorescent, radioactive or chemically labelled, and can bind to the analytes retained on the device according to the invention or can react with them in some other way. Then, the tracer elements retained on the device according to the invention can be identified and optionally quantified by means of an apparatus for detection of fluorescence, colorimetric detection or detection of radioactivity.

It is also possible to base detection on a change of the medium (for example coloration visible to the naked eye) due to a chemical reaction between the tracer element and the analyte, or else between the tracer element (fixed to the analyte) and an additional reagent.

As an illustration, the tracer element can comprise an enzyme that catalyses the formation of a coloured product. It can also comprise beads coated with molecules that can bind to the analytes retained. It is also possible to use labelled antibodies (fluorescent or radioactive) that can attach to antigens present on the analytes.

The detection and optionally quantification of the analytes made possible by the invention in particular find application in medical diagnostics (for human or veterinary medicine).

EXAMPLES

The following examples illustrate but do not limit the invention. Various polymers with a polysaccharide skeleton of dextran are prepared in the examples given below:

the polymer PsAc1 which comprises Ac groups of the —$CH_2COONa$ type;

the polymer PsAcAr1 which comprises Ac groups of the —$CH_2COONa$ type and Ar groups of the —$CH_2CONHCH_2Ph$ type;

the polymer PsAcF1 which comprises Ac groups of the —$CH_2COONa$ type and F groups of the —$CH_2CONH(CH_2)_3N_3$ type;

the polymer PsAcArF1 which comprises Ac groups of the —$CH_2COONa$ type, Ar groups of the —$CH_2CONHCH_2Ph$ type and F groups of the —$CH_2CONHNH_2$ type;

the polymer PsAcArF2 which comprises Ac groups of the —$CH_2COONa$ type, Ar groups of the —$CH_2CONHCH_2Ph$ type and F groups of the —$CH_2CONH(CH_2)_3N_3$ type;

the polymer PsAcF2 which comprises Ac groups of the —$CH_2COONa$ type and F groups of formula (II) above, with $R_4$ representing —$(CH_2)_3OH$;

the polymer PsAcF3 which comprises Ac groups of the —$CH_2COONa$ type and F groups of formula (II) above, with $R_4$ having formula (III) above;

the polymer PsAcArF3 which comprises Ac groups of the —$CH_2COONa$ type, Ar groups of the —$CH_2CONHCH_2Ph$ type and F groups of formula (II) above, with $R_4$ representing —$(CH_2)_3OH$;

the polymer PsAcArF4 which comprises Ac groups of the —$CH_2COONa$ type, Ar groups of the —$CH_2CONHCH_2Ph$ type and F groups of formula (II) above, with $R_4$ having formula (III) above;

the polymer PsAcArF5 which comprises Ac groups of the —$CH_2COONa$ type, Ar groups of the —$CH_2CONHCH_2Ph$ type and F groups of formula (V) above, with X representing $CH_2$ and X' representing $(CH_2)_2$.

The form PsAc (x) denotes a polymer comprising a degree of substitution with Ac groups equal to x.

The form PsAcAr (x; y) denotes a polymer comprising an overall degree of substitution with Ac and Ar groups equal to x and a degree of substitution with Ar groups equal to y.

The form PsAcF (x; z) denotes a polymer comprising an overall degree of substitution with Ac and F groups equal to x and a degree of substitution with F groups equal to z.

The form PsAcArF (x; y; z) denotes a polymer comprising an overall degree of substitution with Ac, Ar and F groups equal to x, a degree of substitution with Ar groups equal to y and a degree of substitution with F groups equal to z.

Example 1

Preparation of the Polymer PsAc1 (General Protocol)

Dextran T40 (2 g, 11.1 mmol, 1 eq) is dissolved in 6.4 mL of deionized water. Isopropanol (36 mL) is added slowly to this solution under very vigorous stirring, then soda (2.4 g, 60 mmol, 5.4 eq), and the reaction mixture is stirred for 1 hour at 60° C. Finally monochloroacetic acid (3 g, 31.7 mmol) is added, then it is stirred overnight at 60° C. The white paste obtained is recovered and precipitated three times from methanol and centrifuged. The solid obtained is dissolved in deionized water and lyophilized to give the polymer PsAc1. Typically, this protocol gives a degree of substitution with the Ac groups from 1.2 to 1.4.

Example 2

Measurement of the Degree of Substitution with Carboxylic Acid Groups

Determination of the degree of substitution with methylcarboxylate groups is carried out by $^1$H NMR after hydrolysis.

For this, the product is hydrolysed as follows:

The polymer PsAc1 (200 mg) is dissolved in 2 mL of $D_2O$, then 666 µL of $D_2SO_4$ is added slowly. The reaction mixture is heated at 90° C. for 4 hours. The mixture is analysed by $^1$H NMR 300 MHz.

The degree of substitution (DS) is calculated from the following equation: DS=N$B$, with A: (½)×integral of the signal of the protons of C$\underline{H}_2CO_2$H between 4 and 4.5 ppm; and B: integral of the protons carried by the carbons $C_1$ of the glucose units, or (⅙)×integral of the protons carried by the carbons $C_{2-6}$ between 3 and 4 ppm.

Example 3

Preparation of the Polymer PsAcAr1

100 mg of PsAc1 (1.1) is dissolved in 2 mL of deionized water, then the pH is adjusted to 4.74 with a 1N HCl solution. 1-cyclohexyl-3-(2-morpholino-ethyl)carbodiimide (CMC) (233 mg, 0.55 mmol, 1.1 eq) is added, then the pH is adjusted again to 4.74 with a 1N HCl solution. Benzylamine is added and the reaction mixture is stirred overnight at ambient temperature. The samples are then dialyzed for 70 hours in a 2M NaCl solution and then for 100 hours in deionized water to give the polymer PsAcAr1.

Example 4

Measurement of the Degree of Substitution with Aromatic Groups

The degree of substitution with aromatic groups is calculated from the $^1$H NMR 300 MHz spectra using the following equation: DS=(B/A)/5, with A: integral of the protons carried by $C_1$; B: integral of the aromatic protons due to the phenyl group.

FIG. 1 illustrates the relationship between the degree of substitution (y) with $CH_2CONHCH_2Ph$ group and the number of benzylamine equivalents (eq) used in the reaction (0.3 eq, 0.6 eq, 1 eq, 2 eq, 5 eq and 15 eq relative to the degree of substitution with available carboxyl groups).

Example 5

Synthesis of 2-(3-azidopropyl)-isoindole-1,3-dione

N-(3-Bromopropyl)phthalimide (15 g, 56.02 mmol) is dissolved in 200 mL of dimethylformamide, then sodium nitride is added (7.25 g, 112.05 mmol, 2 eq). Stirring is maintained for 2 hours at 70° C. The reaction mixture is then evaporated to dryness and then co-evaporated with toluene to remove the traces of dimethylformamide. The residue obtained is solubilized in diethyl ether (150 mL), and the organic phase is washed with water (2×150 mL). The organic phase is dried over anhydrous magnesium sulphate. The solvent is evaporated off to give 2-(3-azidopropyl)-isoindole-1,3-dione in the form of a white powder (12.44 g, 54.1 mmol, 97%).

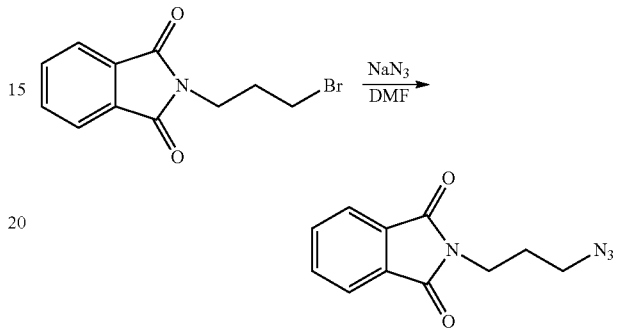

$^1$H NMR (CDCl$_3$, 300 MHz): δ ppm 7.78 (m, 2H), 7.65 (m, 2H), 3.72 (t, 2H, J=6.9 Hz), 3.31 (t, 2H, J=6.9 Hz), 1.90 (tt, 2H, J=6.9 Hz).

$^{13}$C NMR (75 MHz CDCl$_3$): δ ppm 168.28, 134.04, 131.96, 123.31, 49.0, 35.35, 28.0; MALDI-TOF: $M_{calculated}$=230.08 ($C_{11}H_{10}N_4O_2$). found (m/z) 231.1 [M+H]$^+$, 253.1 [M+Na]$^+$.

Example 6

Synthesis of 3-azidopropylamine 2-(3-azidopropyl)-isoindole-1,3-dione (3 g, 12 mmol) is dissolved in 10 mL of dichloromethane, then hydrazine (9.6 mL, 32 mmol, 2.6 eq) is added. The reaction mixture is heated overnight under reflux under stirring. Then a 1N aqueous solution of hydrochloric acid (100 mL) is added. The organic phase is decanted and then the aqueous phase is washed with dichloromethane (3×50 mL). The pH of the aqueous phase is adjusted to 14 with a saturated soda solution. The aqueous phase is then extracted with dichloromethane (3×40 mL). The dichloromethane phases are combined and extracted with a 1N aqueous solution of hydrochloric acid (3×50 mL). The acidic aqueous solution is finally frozen and lyophilized. 3-azidopropylammonium hydrochloride is obtained in the form of a white powder (1.49 g, 10.97 mmol, 84%).

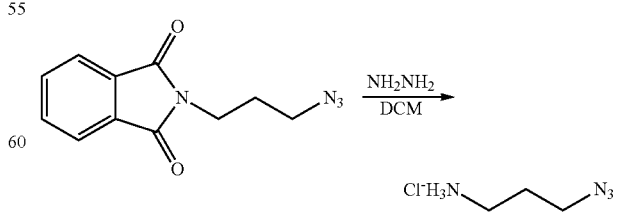

$^1$H NMR (D$_2$O, 300 MHz): δ ppm 3.52 (t, 2H, J=6.6 Hz), 3.11 (t, 2H, J=7.2 Hz), 1.96 (tt, 2H, J=6.6 Hz).

$^{13}$C NMR (D$_2$O, 75 MHz): δ ppm 39.02, 26.48, 15.67.

MALDI-TOF: $M_{calculated}$=100.07 ($C_3H_8N_4$). found m/z 101.0 [M+H]$^+$, 123.0 [M+Na], 139.0 [M+K]+, 107.1 [M+Li]$^+$.

Example 7

Preparation of the Polymer PsAcF1

100 mg of PsAc1 (1.4) is dissolved in 2 mL of deionized water, then the pH is adjusted to 4.74 with a 1N HCl solution. Then 1-cyclohexyl-3-(2-morpholino-ethyl)carbodiimide (CMC) (296.5 mg, 0.7 mmol, 1.1 eq) is added and the pH is adjusted again to 4.74 with a 1N HCl solution. 3-azidopropylamine in the form of hydrochloride is added, then the pH is adjusted to 8.4. The reaction mixture is stirred overnight at ambient temperature. The samples are then dialyzed for 70 hours in a 2M NaCl solution and then for 100 hours in deionized water. Finally, the product PsAcF1 thus obtained is frozen and lyophilized.

Example 8

Measurement of the Degree of Substitution with Reactive Groups

The degree of substitution with azide groups is calculated from the following equation: DS=(B/A)/2, with A: integral of the protons carried by the carbons $C_1$; B: integral of the protons in the strong field (due to the signals of the protons of 3-azidopropylamine).

Figure 2:
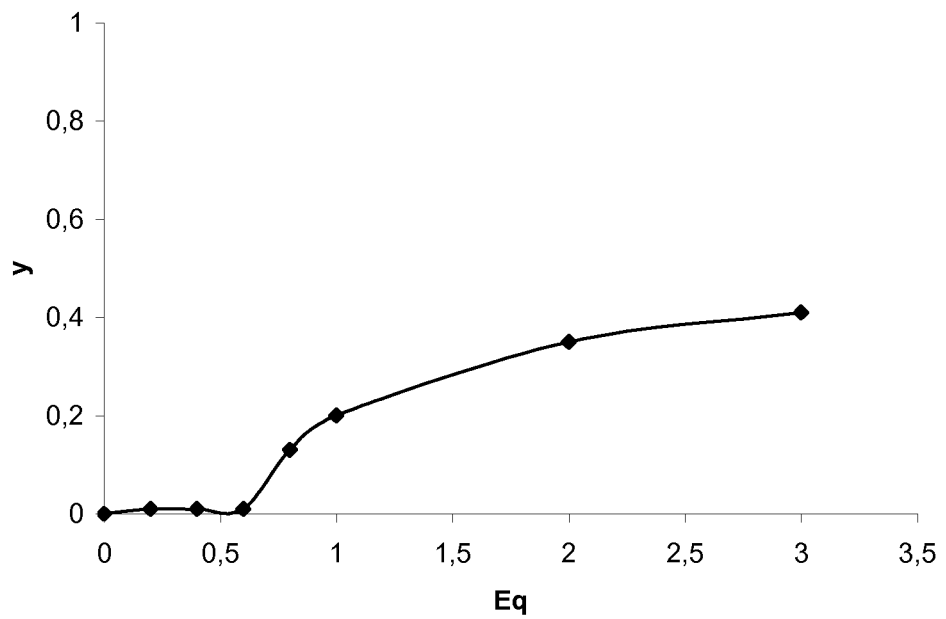
FIG. 2 shows the relationship between the degree of substitution with azide groups (on the y axis) in the polymer PsAcF1 from Example 7, relative to the number of amine azide equivalents (on the x axis). This will be referred to in Example 8.

FIG. 2 illustrates the relationship between the degree of substitution with azide groups (y) and the number of equivalents of 3-azidopropylamine (Eq) used in the reaction, relative to the degree of substitution with available carboxyl groups.

Example 9

Preparation of the Polymer PsAc1 (1.15)

90 mL of isopropanol is added dropwise, under vigorous stirring, to a solution of 5 g (27.7 mmol, 1 eq) of dextran T40 dissolved in 16 mL of water. 6 g (150 mmol, 5.4 eq) of soda is added to the reaction mixture, which is then stirred at 60° C. for 1 h.

7.5 g (79.36 mmol, 2.8 eq) of monochloroacetic acid is then added to this mixture. It is then stirred at 60° C. overnight. A whitish paste is obtained, which is solubilized in 50 mL of water. The product is then precipitated from 500 mL of MeOH cooled to 0° C., under vigorous stirring. The pellets obtained after centrifugation (2500 r.p.m., 10 min, 4° C.) are solubilized in the minimum amount of water and the product is precipitated a second time from 500 mL of MeOH. The pellets obtained after the second precipitation are washed twice with MeOH and are then solubilized in the minimum amount of water and lyophilized. 3 g (15.7 mmol) of PsAc1 with a degree of substitution of 1.15 is obtained, i.e. PsAc1 (1.15).

Example 10

Preparation of the Polymer PsAcAr1 (1.15; 0.64)

The pH of a solution containing 468 mg (2.44 mmol, 1 eq) of PsAc1 (1.15) dissolved in 9.4 mL of water is adjusted to 4.74 by adding 1N and 0.1N HCl. 1.187 g (2.806 mmol) of CMC is added to this solution, the pH is again adjusted to 4.74. 266 µL (2.44 mmol, 1 eq relative to x) of benzylamine is then added to the reaction mixture, which is stirred with a magnetic stirrer overnight at ambient temperature. The final pH of the solution is 10.2.

The reaction mixture is then introduced into dialysis tubing (3500 g/mol; 1 mL/cm), which is immersed in 3.5 L of a 2M NaCl solution, where it remains for 5 days, and then in 3.5 L of water, where it remains, also for 5 days.

The contents of the bag are then put in a pot, to be frozen and then lyophilized. 477 mg (1.67 mmol) of PsAcAr1 (1.15; 0.64) is obtained (degree of substitution with benzylamino group 0.64).

Example 11

Preparation of the Polymer PsAcArF1 (1.15; 0.64; 0.26)

The pH of a solution containing 256 mg (0.895 mmol, 1 eq) of PsAcAr1 (1.15; 0.64) dissolved in 2 ml of water is adjusted to 4.74 by adding 1N and 0.1N HCl. 212.5 mg (0.502 mmol) of CMC is added to this solution, the pH is again adjusted to 4.74. 870 µL (4.56 mmol) of a solution of hydrazine at 24-26% in water is then added to the reaction mixture, which is stirred with a magnetic stirrer overnight at ambient temperature. The final pH of the solution is 10.28.

The reaction mixture is then put in dialysis tubing (3500 g/mol; 1 mL/cm), which is immersed in 3.5 L of a 2M NaCl solution, where it remains for 5 days, and then in 3.5 L of water, where it remains, also for 5 days.

The contents of the bag are then put in a pot, to be frozen and then lyophilized. 235 mg (0.81 mmol) of PsAcArF1 (1.15; 0.64; 0.26) is thus obtained (degree of substitution with hydrazide 0.26).

Example 12

Preparation of the Polymer PsAcAr1 (1.2; 0.49)

The pH of a solution of 513.3 mg of PsAc1 (1.2), dissolved in 10 mL of deionized water, is adjusted to 4.74 with a 1N hydrochloric acid solution. N-cyclohexyl-N'-(2-morpholinoethyl)-carbodiimide methylsulphonate (931.85 mg, 2.2 mmol, 1.1 eq.) is added at ambient temperature, then the pH of the solution is adjusted to 4.74 in the same way. Benzylamine (428.6 mg, 4.0 mmol, 2 eq.) is then added dropwise and the solution is stirred at ambient temperature for 16 hours. The reaction mixture is purified by dialysis in a 2M NaCl solution for 3 days, then in deionized water for 3 days. After lyophilization, PsAcAr1 (1.2; 0.49) is obtained in the form of an amorphous white powder (degree of substitution with benzylamino groups 0.49).

$^1$H NMR ($D_2O$, 300 MHz): δ (ppm): 7.21 (s, Is, $H_{ar}$), 5.09 (s, Is, $H_{ano}$), 4.89 (s, Is, $H_{ano}$), 4.53-3.39 (m, Is).

Example 13

Preparation of the Polymer PsAcF1 (1.2; 0.38)

513.3 mg of PsAc1 (1.2) is dissolved in 10 mL of deionized water. The pH of the solution is adjusted to 4.74 with a 1N HCl solution. N-cyclohexyl-N'-(2-morpholino-ethyl)-carbodiimide methylsulphonate (931.85 mg, 2.2 mmol, 1.1 eq.) is added to the solution and the pH is adjusted again to 4.74. 3-azidopropylammonium hydrochloride (819.5 mg, 6 mmol, 3 eq.) is added to the reaction mixture, then the pH is adjusted to 8.4 with a 1N $Na_2CO_3$ solution.

The reaction mixture is stirred at ambient temperature for 16 hours. The crude product is dialyzed for 3 days in a 2M NaCl solution and then for 3 days in deionized water. Lyophilization gives PsAcF1 (1.2; 0.38) in the form of an amorphous white powder (degree of substitution with azido groups 0.38).

$^1$H NMR (D$_2$O, 300 MHz): δ (ppm): 5.07 (s, Is, H$_{ano}$), 4.88 (s, Is, H$_{ano}$), 4.28-3.26 (m, Is), 1.77 (s, Is, CH$_2$).

Example 14

Preparation of the Polymer PsAcArF2 (1.2; 0.34; 0.38)

A solution of 272.2 mg of PsAcF1 (1.2; 0.38) dissolved in 5 mL of deionized water is adjusted to pH 4.74 with a 1N HCl solution. N-cyclohexyl-N'-(2-morpholinoethyl)-carbodiimide methylsulphonate (372.8 mg, 0.88 mmol, 1.1 eq.) is added and the pH of the reaction mixture is adjusted again to 4.74 with a 1N HCl solution. Benzylamine (171.4 mg, 4.6 mmol, 2 eq.) is added and the solution is stirred at ambient temperature for 18 hours. Dialysis in 2N NaCl for 3 days, then in deionized water for 3 days, followed by lyophilization, gives the compound PsAcArF2 (1.2; 0.34; 0.38) (degree of substitution with benzylamino group 0.34).

$^1$H NMR (D$_2$O, 300 MHz): δ (ppm): 7.23 (s, Is, H$_{ar}$), 5.05 (s, Is, H$_{ano}$), 4.84 (s, Is, H$_{ano}$), 4.33-3.26 (m, Is), 1.68 (s, Is, CH$_2$).

Example 15

Preparation of the Polymer PsAcArF2 (1.2; 0.49; 0.62)

N-cyclohexyl-Ar-(2-morpholinoethyl)-carbodiimide methylsulphonate (372.7 mg, 0.88 mmol, 1.1 eq.) is added to a solution of 224.2 mg of PsAcAr1 (1.2; 0.49) in 5 mL of deionized water at pH=4.74. The pH of the solution is adjusted to 4.74 with a 1N HCl solution, and then 3-azidopropylammonium hydrochloride (327.8 mg, 2.4 mmol, 3 eq.) is added. The pH is adjusted to 8.4, then the solution is stirred at ambient temperature for 17 hours. Dialysis in 2N NaCl for 3 days, then in deionized water for 3 days, and finally lyophilization, gives the polymer PsAcArF2 (1.2; 0.49; 0.62) (degree of substitution with azide group 0.62).

$^1$H NMR (D$_2$O, 300 MHz): δ (ppm): 7.23 (s, Is, H$_{ar}$), 5.05 (s, Is, H$_{ano}$), 4.84 (S, Is, H$_{ano}$), 4.33-3.26 (m, Is), 1.68 (s, Is, CH$_2$).

Example 16

Synthesis of pent-4-ynyl-α-D-glucopyranoside

The product of formula (VIII) is synthesized as described below:

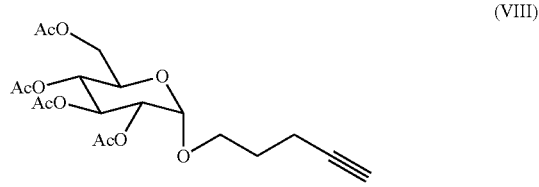 [SMILES: C#CCCCOC1OC(COC(C)=O)C(OC(C)=O)C(OC(C)=O)C1OC(C)=O]

(VIII)

D-(+)-glucose (360.3 mg, 2.0 mmol) is dissolved in 4-pentyn-1-ol (1.01 g, 12.0 mmol, 6.0 eq.) and the solution is heated to 65° C. 120 mg of H$_2$SO$_4$—SiO$_2$ is added and the solution is stirred at 65° C. for 10 hours. The solution is cooled to ambient temperature and then the compound is purified by silica gel chromatography with a gradient from CH$_2$Cl$_2$ to CH$_2$Cl$_2$-MeOH; 9:1, as eluent mixture. The desired product is obtained in the form of colourless oil with a yield of 79% and an anomeric ratio α/β of 1.6/1. The residue (405.0 mg, 1.63 mmol) is dissolved in pyridine (5 mL) and acetic anhydride (1.33 g, 13.0 mmol, 8 eq.) at ambient temperature.

DMAP (20 mg) is then added at 0° C. and the reaction mixture is stirred at ambient temperature for 5 hours. The reaction mixture is neutralized by the dropwise addition of 5 mL of MeOH at 0° C. The solvents are removed under reduced pressure in a rotary evaporator and the residual solvents are co-evaporated 3 times with toluene. Purification by silica gel chromatography with pentane-EtOAc (8/2) eluent mixture gives 190 mg of white crystals of the desired tetraacetylated product of a conformation as well as 450 mg of a mixture of the two anomers, corresponding to a total yield of 98%:

$^1$H NMR (D$_2$O, 300 MHz): δ (ppm): 5.47 (dd, 1H, J=10.0, 9.6 Hz), 5.06 (m, 2H), 4.87 (dd, 1H, J=10.2, 3.7 Hz), 4.27 (dd, 1H, J=12.3, 4.3 Hz), 4.07 (m, 2H), 3.85 (dt, 1H, J=9.9, 5.9 Hz), 3.54 (dt, 1H, J=9.9, 6.1 Hz), 2.34 (dt, 2H, 1H, J=6.8, 2.7 Hz), 2.10 (s, 3H), 2.07 (s, 3H), 2.03 (s, 3H), 2.02 (s, 3H), 1.97 (t, 1H, J=2.6 Hz), 1.82 (q, 2H, J=6.5 Hz).

$^{13}$C NMR (D$_2$O, 75 MHz): δ (ppm): 170.9, 170.4, 170.3, 169.8, 96.1, 83.3, 71.0, 70.4, 69.4, 68.9, 68.7, 67.4, 66.9, 62.1, 28.4, 20.9, 20.9, 20.8, 20.8, 15.2. HRMS calculated for C$_{19}$H$_{26}$O$_{10}$ [M+Na]$^+$: 437.5; found m/z: 437.1.

Example 17

Synthesis of pent-4-ynyl-α-D-glucopyranoside

The product of formula (IX) is synthesized as described below:

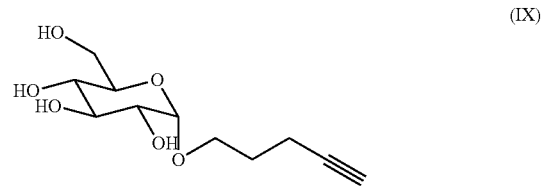 [SMILES: C#CCCCOC1OC(CO)C(O)C(O)C1O]

(IX)

4 mL of NaOMe at 0.1 M in MeOH is added at 0° C. to a solution of the tetraacetylated compound obtained in Example 16 (180 mg, 0.434 mmol) dissolved in 3 mL of MeOH, and the reaction mixture is stirred at ambient temperature for 4 hours. The reaction mixture is then neutralized to pH=7 with Dowex-50W resin. The reaction mixture is then filtered, evaporated to dryness under reduced pressure and purified by silica gel column chromatography with CH$_2$Cl$_2$-MeOH; 9:1 as eluent to give the derivative of α-glucose at a quantitative yield in the form of colourless oil.

$^1$H NMR (D$_2$O, 300 MHz): δ (ppm): 5.12 (d, 1H, J=3.9 Hz), 4.08 (m, 2H), 4.00 (m, 1H), 3.92 (m, 2H), 3.82 (m, 1H), 3.76 (m, 1H), 3.62 (m, 1H), 2.55 (m, 3H), 2.03 (m, 2H). $^{13}$C NMR (D$_2$O, 75 MHz): δ (ppm): 100.0, 87.0, 75.1, 73.6, 73.3, 71.6, 71.4, 68.2, 62.4, 29.3, 16.5. HRMS calculated for $C_{11}H_{18}O_6$ [M+Na]$^+$: 269.1; found m/z: 269.0

Example 18

Preparation of the Polymer PsAcF2 (1.2; 0.4)

The polymer PsAcF1 (1.2; 0.4) (24.8 mg) and 4-pentyn-1-ol (200 µL of a solution at 92.5 mg/mL in water, 0.22 mmol, 2.2 eq.) are stirred in 150 µL of deionized water at ambient temperature. Sodium ascorbate (50 µL of a freshly prepared solution in water at 200 mg/mL, 0.05 mmol, 0.5 eq.), and pentahydrated copper(II) sulphate (50 µL of a solution at 25 mg/mL in water, 0.005 mmol, 0.05 eq.) are then added to the reaction mixture, which is mixed at ambient temperature for 20 hours. Purification by dialysis in a 2M NaCl solution for 3 days, then in deionized water for 3 days followed by lyophilization gives the polymer PsAcF2 (1.2; 0.4) in the form of an amorphous white powder. The degree of substitution with triazole is 0.4 (i.e. essentially all the reactive Ar groups were converted).

$^1$H NMR (D$_2$O, 300 MHz): δ (ppm): 7.65 (s, Is, H$_{triazole}$), 5.03 (s, Is, H$_{ano}$), 4.85 (s, Is, H$_{ano}$), 4.30-3.30 (m, Is), 3.13 (s, Is, CH$_2$), 2.61 (s, Is, CH$_2$), 2.01 (s, Is, CH$_2$), 1.75 (s, Is, CH$_2$).

Example 19

Preparation of the Polymer PsAcF3 (1.2; 0.34)

Sodium ascorbate (50 µL of a freshly prepared solution in water at 200 mg/mL, 0.05 mmol, 0.5 eq.), and then pentahydrated copper(II) sulphate (50 µL of a solution at 25 mg/mL in water, 0.005 mmol, 0.05 eq.) are added successively to a mixture of PsAcF1 (1.2; 0.34) (24.8 mg) and pent-4-ynyl-α-D-glucopyranoside (49.3 mg, 0.2 mmol, 2.0 eq.) in 900 µL of deionized water at ambient temperature. After 20 hours, the reaction mixture is purified by dialysis in a 2M NaCl solution for 3 days, then in deionized water for 2 days. The polymer PsAcF3 (1.2; 0.34) is obtained after lyophilization in the form of an amorphous white powder. The degree of substitution with triazole is 0.26, i.e. only some of the reactive F groups were converted.

$^1$H NMR (D$_2$O, 300 MHz): δ (ppm): 7.74. (s, Is, H$_{triazole}$), 5.06 (s, Is, H$_{ano}$), 4.88 (s, Is, H$_{ano}$), 4.78 (s, Is, H$_{ano}$), 4.34-3.16 (m, Is), 2.71 (s, Is, CH$_2$), 2.05 (s, Is, CH$_2$), 1.89 (s, Is, CH$_2$).

Example 20

Preparation of the Polymer PsAcArF3 (1.2; 0.42; 0.38)

Sodium ascorbate (50 µL of a freshly prepared solution in water at 200 mg/mL, 0.05 mmol, 0.5 eq.), and then pentahydrated copper(II) sulphate (50 µL of a solution at 25 mg/mL in water, 0.005 mmol, 0.05 eq.) are added successively to a mixture of PsAcArF2 (1.2; 0.42; 0.38) (28.7 mg) and 4-pentyn-1-ol (200 µL of a solution at 92.5 mg/mL in water, 0.22 mmol, 2.2 eq.) in 700 µL of deionized water at ambient temperature. After 20 hours, the reaction mixture is purified by dialysis in a 2M NaCl solution for 3 days, then in deionized water for 2 days. The polymer PsAcArF3 (1.2; 0.42; 0.38) is obtained after lyophilization in the form of an amorphous white powder. The degree of substitution with triazole is 0.28 (degree of conversion 74% of the reactive F groups).

$^1$H NMR (300 MHz, D$_2$O) δ (ppm): 7.62 (s, Is, H$_{triazole}$) 7.21 (s, Is, H$_{ar}$), 5.04 (s, Is, H$_{ano}$), 4.89 (S, Is, H$_{ano}$), 4.29-3.50 (m, Is), 3.13 (s, Is, CH$_2$), 2.58 (s, Is, CH$_2$), 1.96 (s, Is, CH$_2$), 1.73 (s, Is, CH$_2$).

Example 21

Preparation of the Polymer PsAcArF4 (1.2; 0.42; 0.38)

Sodium ascorbate (100 µL at 200 mg/mL in PBS, 0.05 mmol, 1 eq.) is added to a solution of PsAcArF2 (1.2; 0.42; 0.38) (28.7 mg) and pent-4-ynyl-α-D-glucopyranoside (43.8 mg, 0.178 mmol, 1.8 eq.) in 500 µL of deionized water and 400 µL of PBS at 0.1 M. Pentahydrated copper(II) sulphate (100 µL of 25 mg/mL in PBS, 0.005 mmol, 0.1 eq.) is added and the reaction mixture is stirred at ambient temperature for 20 h. The dextran is taken up in an aqueous solution of EDTA-2Na at 0.5 M (2 mL) before being purified by dialysis in a 2M NaCl solution for 3 days, then in deionized water for 2 days. Lyophilization gives PsAcArF4 (1.2; 0.42; 0.38) in the form of an amorphous white powder. The degree of substitution with triazole is 0.34 (degree of conversion of 89% of the reactive F groups).

$^1$H NMR (300 MHz, D$_2$O) δ (ppm): 7.63 (s, Is, H$_{triazole}$), 7.21 (s, Is, H$_{ar}$), 5.00 (s, Is, H$_{ano}$), 4.90 (S, Is, H$_{ano}$), 4.85 (s, Is, H$_{ano}$), 4.23-3.22 (m, Is), 3.09 (s, Is, CH$_2$), 2.64 (s, Is, CH$_2$), 1.22 (s, Is, CH$_2$), 1.19 (s, Is, CH$_2$).

Example 22

Functionalization of Polystyrene Plates and Measurement of the Contact Angle

A polystyrene plate (Goodfellow plate, 10 cm×10 cm), washed beforehand with water and with ethanol, is half-immersed in a solution of polymer in PBS buffer at a concentration of 10 µg/mL or in PBS alone (control) overnight at ambient temperature (one plate per type of polymer). The polymers tested are those described above and more particularly PsAc1 (1.2), PsAcAr1 (1.2; 0.42), PsAcArF2 (1.2; 0.42; 0.38) and PsAcArF4 (1.2; 0.42; 0.27) (the value of 0.27 representing here only the degree of substitution with triazole).

The polystyrene surface in contact with the solution is then immersed twice for 5 minutes in a water bath. It is dried under nitrogen for 10 min.

These surfaces are then used for measurements of the contact angle. The zone of the substrate that has not been in contact with the solution is used as control.

Figure 3:
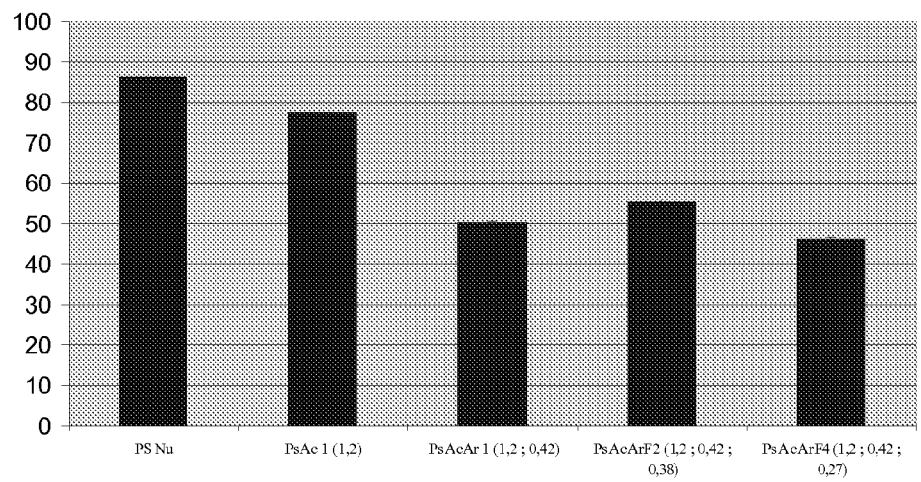
FIG. 3 is a histogram showing measurements of contact angles (in degrees) on functionalized or unfunctionalized polystyrene plates. This will be referred to in Example 22.

Ten 1-µL drops of water are deposited in the middle of the treated and untreated (control) surface. The results (median of the angle and interquartile range) are shown in FIG. 3.

It can be seen that treatment of the polystyrene surface with the polysaccharides PsAcAr1, PsAcArF2 and PsAcArF4 leads to a significant decrease in the contact angle of water compared with untreated polystyrene. These polymers therefore permit functionalization of polystyrene.

Example 23

Functionalization of 96-Well Polystyrene Plates with Ligands

In this example, the bottom of polystyrene wells is completely covered with a layer of PsAc, PsAcAr or PsAcArF and then incubated with ligands (lectins). A protein is then incubated with the ligand-functionalized surface.

Finally, a fluorescence detection system makes it possible to identify the wells that have captured the target protein.

The 96-well plates used are of the MaxiSorp Immunoplate type from the manufacturer Nunc.

1) 100 μL of a solution of polymer in PBS (pH=7.4) (between 50 μg/mL and 0.1 μg/mL) is incubated in the wells of the plate for 16 h at ambient temperature.

2) The wells are then washed with 3×300 μL of PBS (pH=7.4) containing 0.1% of Tween 20 for 3×5 minutes.

3) The wells are then incubated with 300 μL of a solution of PBS (pH=7.4) Tween 20 (0.1%) containing BSA (3%, 1% or 0.1%) or casein (0.1%) for 1 hour at ambient temperature.

4) The wells are washed with 3×300 μL of PBS (pH=7.4) Tween 20 (0.1%) for 3×5 minutes.

5) The wells are then incubated with 200 μL of a solution of biotinylated lectin (for example 10 μg/mL, 5 μg/mL or 1 μg/mL) in PBS (pH=7.4) Tween 20 (0.1%) containing $MnCl_2$ and $CaCl_2$ at a final concentration of 1 mM. Incubation takes 1 hour at ambient temperature under stirring.

The following lectins (commercially available) were used: concanavalin A (ConA), wheat germ agglutinin (WGA) and Erythrina cristagalli lectin (ECL). ConA interacts with terminal alpha-D-glucose or alpha-D-mannose residues. WGA recognizes the N-acetyl-D-glucosamines. ECL recognizes the terminal alpha-D-galactose residues.

6) The wells are washed with 3×300 μL of PBS (pH=7.4) Tween 20 (0.1%) for 3×5 minutes.

7) The wells are then incubated with 200 μL of a solution of tetramethylrhodamine-labelled streptavidin (5 μg/mL or 1 μg/mL) in PBS (pH=7.4) Tween 20 (0.1%) for 2 hours at ambient temperature.

8) The wells are washed with 3×300 μL of PBS (pH=7.4) Tween 20 (0.1%) for 3×5 minutes.

9) The wells are washed with 3×300 μL of deionized water for 3×5 minutes.

10) The plate is dried in the centrifuge for 10 min and then dried under nitrogen for 5 min.

11) The fluorescence at the bottom of the wells is measured at 532 nm using a confocal fluorescence scanner.

Figure 4:
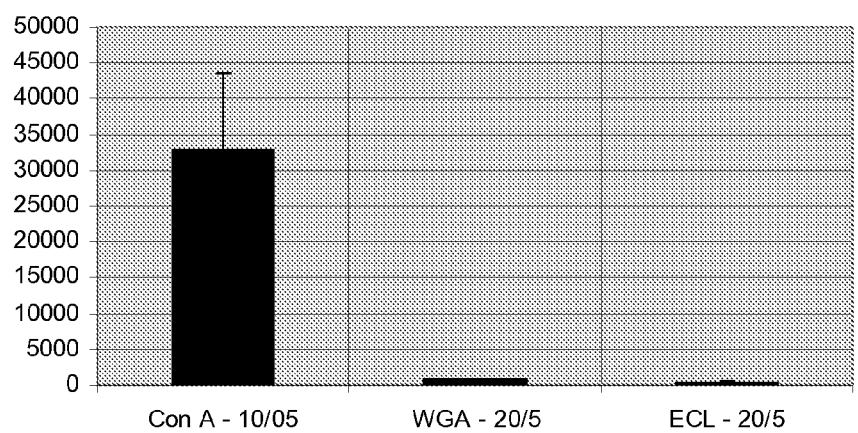
FIGS. 4, 5 and 6 illustrate the specificity of fixation of concanavalin A (relative to other lectins) on a polymer according to the invention. This will be referred to in Examples 23 and 24.
Figure 5:
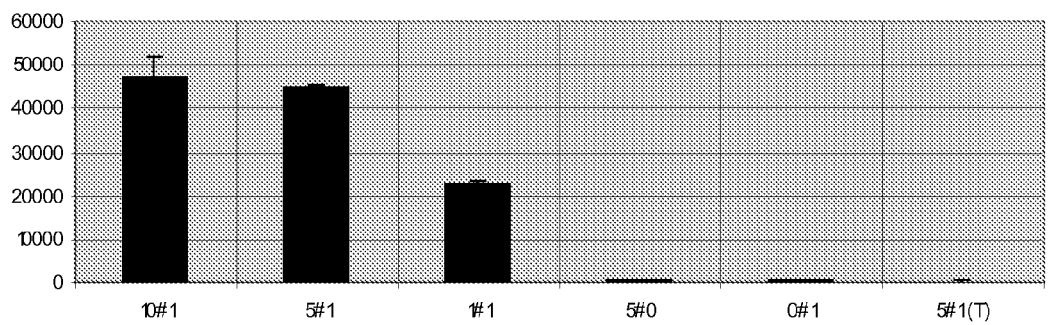

The results are shown in FIGS. 4 and 5.

FIG. 4 is a histogram showing the intensity of fluorescence obtained with the polymer PsAcArF4 (1.2; 0.42, 0.34) (the degree of substitution of 0.34 only relating to the triazole F groups) and the three lectins mentioned above. The ratios shown on the x axis are the lectin/streptavidin ratios.

It can be seen that PsAcArF4 is recognized selectively by ConA as expected, showing the quality of functionalization of the polystyrene plate and the availability of the ligand with respect to the target protein.

FIG. 5 is a histogram showing the intensity of fluorescence obtained with the same polymer PsAcArF4 (1.2; 0.42, 0.34) and ConA. The ratios shown on the x axis are the lectin/streptavidin ratios. The last result (T) is a control without the polysaccharide.

This experiment illustrates the relationship between the intensity of the fluorescence signal and the concentration of ConA used in the wells. The fluorescence associated with the wells that did not receive ConA, streptavidin or PsAcArF4 is very low.

Example 24

Formation of Microdots at the Bottom of the Wells of a 96-Well Plate by Printing of Polysaccharides, Interaction with the Lectins In this experiment, various polymers are printed at the bottom of an untreated 96-well plate.

The biochips thus produced are then incubated with proteins (lectins).

The 96-well plates used are of the MaxiSorp Immunoplate types from the manufacturer Nunc. 300 μL of polymer solution (at concentrations of 10 μg/mL, 7.5 μg/mL, 5 μg/mL and 1 μg/mL in PBS) are deposited on the plate using a Packard BioChipArrayer BCA-1 apparatus in the following arrangement:

PsAcArF4 (1.2; 0.42; 0.27)
PsAcF1 (1.2; 0.38)
PsAcArF2 (1.2; 0.42; 0.38)

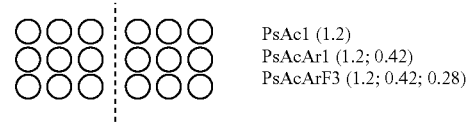

PsAc1 (1.2)
PsAcAr1 (1.2; 0.42)
PsAcArF3 (1.2; 0.42; 0.28)

For the polymer PsAcArF4, the degree of substitution of 0.27 corresponds to the triazole groups only. For the polymer PsAcArF3 the degree of substitution of 0.28 corresponds to the triazole groups only.

1) The wells are then incubated with 100 μL of a solution of PBS (pH=7.4) Tween 20 (0.1%) containing BSA (3%) for 15 minutes at ambient temperature.

2) The wells are then washed with 3×100 μL of PBS (pH=7.4) containing 0.1% of Tween 20 for 3×5 minutes.

3) The wells are then incubated with 100 μL of a solution of biotinylated lectin (for example 20 μg/mL, 10 μg/mL or 5 μg/mL) in PBS (pH=7.4) Tween 20 (0.1%) for 1 hour at ambient temperature under orbital stirring. For the lectins (ConA, ECL and WGA), salts of $MnCl_2$ and $CaCl_2$ are added for a final concentration of 1 mM.

4) The wells are washed with 3×100 μL of PBS (pH=7.4) Tween 20 (0.1%) for 3×5 minutes.

5) The wells are then incubated with 100 μL of a solution of streptavidin tetramethylrhodamine (5 μg/mL) in PBS (pH=7.4) Tween 20 (0.1%) for 2 hours at ambient temperature.

6) The wells are washed with 3×100 μL of PBS (pH=7.4) Tween 20 (0.1%) for 3×5 minutes.

7) The wells are washed with 3×100 μL of deionized water for 3×5 minutes.

8) The plate is dried in the centrifuge for 10 min and then dried under nitrogen for 5 min. 9) Detection is carried out with the scanner at 532 nm.

Figure 6:
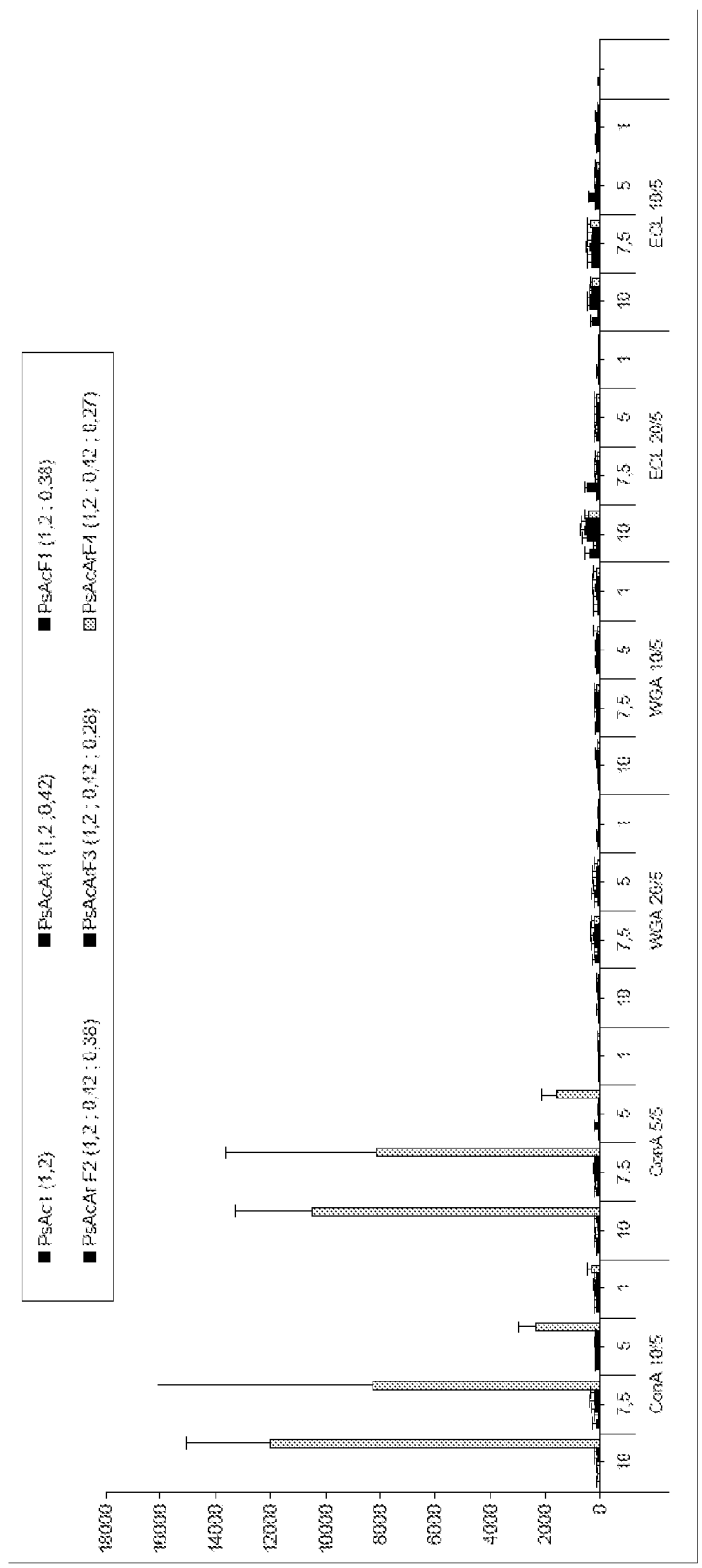

FIG. 6 summarizes the results obtained. It can be seen that ConA is fixed selectively on the polymer PsAcArF4, neither of the other two lectins being fixed.

Example 25

Functionalization of Polystyrene Plates and Measurement of the Contact Angle, Influence of the Degree of Aromatic Substitution The polymers PsAc1 (1.27), PsAcAr1 (1.27; 0.03), PsAcAr1 (1.27; 0.39) and PsAcAr1 (1.27; 0.54) are used for this experiment.

Five polystyrene plates (Goodfellow plates, 10 cm×10 cm), washed beforehand with water and with ethanol, are half-immersed in the solutions of PsAc1 or PsAcAr1 dissolved in PBS buffer at a concentration of 10 µg/mL or in PBS alone, overnight at ambient temperature.

The polystyrene surface in contact with the solution is then immersed twice for 5 minutes in a water bath. It is then dried under nitrogen for 10 min.

These surfaces are then used for measurements of the contact angle. The zone of the substrate that was not in contact with the solution is used as control.

Ten 1-µL drops of water are deposited in the middle of the treated and untreated (control) surface.

Figure 7:
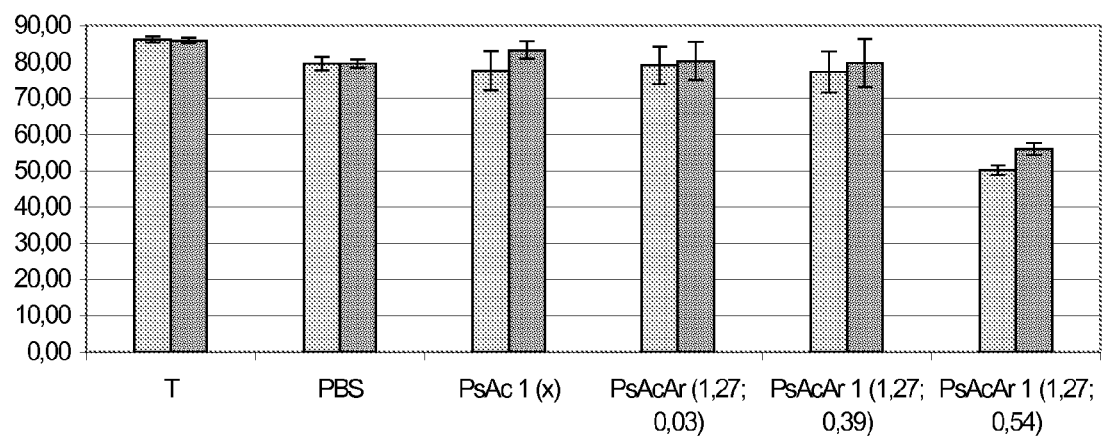
FIG. 7 is a histogram illustrating the influence of the degree of aromatic substitution on the contact angle (in degrees) on functionalized polystyrene plates. This will be referred to in Example 25.

The results (median of the angle and interquartile range) are shown in FIG. 7. The first bar is the result of immediate measurement, and the second bar after storage for 24 h under partial vacuum (desiccator).

It can be seen that PsAcAr1 (1.27; 0.54) allows a significant decrease in contact angle, which decreases from 86° for the untreated polystyrene to 56° for the treated polystyrene. The functions grafted on the polystyrene surface by means of PsAcAr1 (1.27; 0.54) make the surface more hydrophilic, which is reflected in a decrease in the contact angle of water on these surfaces, relative to the untreated polystyrene. The polymer PsAcAr1 (1.27; 0.54) thus allows chemical functionalization of polystyrene.

Example 26

Functionalization of 96-Well Polystyrene Plates and Hydrazone Ligation with Fluorescent Peptides The polymers PsAcArF1 (1.1; 0.75; 0.03) and PsAcAr1 (1.1; 0.75) are used for this experiment. The polymer PsAcArF1 (1.1; 0.75; 0.03) makes it possible to functionalize the bottom of the wells with a hydrazide function. The polymer PsAcAr1 (1.1; 0.75), which does not bear this function, serves as control. The hydrazide function is known to react with molecules bearing an aldehyde function. The bond formed is a hydrazone. The principle of the reaction is as follows:

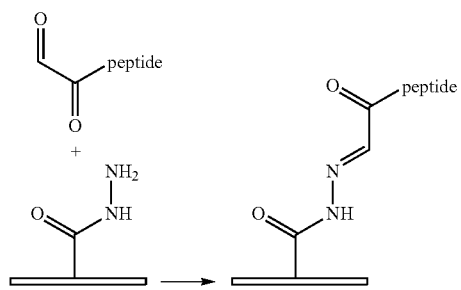

Two peptides are used: peptide 1 (SEQ ID NO: 1) of formula Rho-KR—NH(CH$_2$)$_3$—NH—CHOCO (functionalized with tetramethylrhodamine and with a CHOCO function) and peptide 2 (SEQ ID NO: 2) of formula Rho-KR—NH$_2$ (functionalized with tetramethylrhodamine and with an amide function). The synthesis of these peptides is described in Ollivier et al., *Alpha-oxo semicarbazone peptide or oligodeoxynucleotide microarrays*, Bioconjug. Chem. 14, 430-9 (2003).

Protocol:

The wells of a 96-well polystyrene microplate (Maxisorp, Nunc) are treated with 100 µL of a solution of PsAcArF1 (1.1; 0.75; 0.03) or of PsAcAr1 (1.1; 0.75) at a concentration of 5 µg/mL in PBS. The treatment is carried out at ambient temperature under stirring overnight.

The plate is then washed with PBS/Tween 20 0.05% using a plate washer (300 µL/well, 6 washings).

Two series of solutions of peptides 1 and 2 are prepared at concentrations of $10^{-6}$, $5 \times 10^{-7}$, $2.5 \times 10^{-7}$, $1.25 \times 10^{-7}$ and $6.25 \times 10^{-8}$ M in an acetate buffer pH 5.5/0.1% of BSA. 60 µL of each solution is deposited at the bottom of the wells treated with PsAcArF1 (1.1; 0.75; 0.03) or PsAcAr1 (1.1; 0.75) (2 wells/condition). The ligation reaction is carried out with stirring for 2 h at ambient temperature.

The plate is washed with PBS/Tween 20 (0.05%) (300 µL/well, 6 washings) and then with deionized water (300 µL/well, 3 washings). Drying in the centrifuge is then carried out (2500 r.p.m., 5 min, 20° C.). The plate is read in a Tecan fluorescence scanner.

Figure 8:
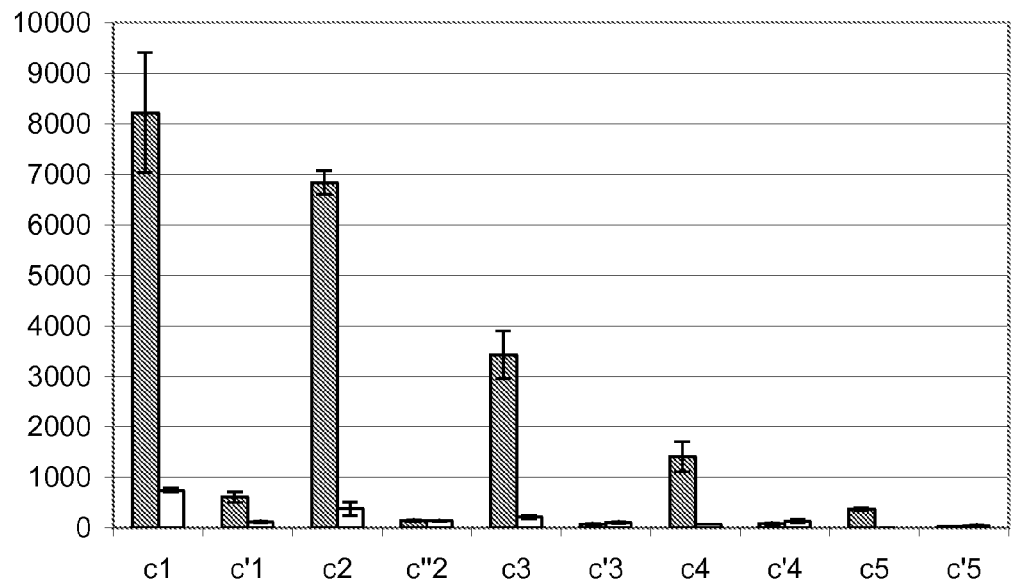
FIG. 8 is a histogram illustrating the chemoselective binding of a peptide aldehyde to a surface functionalized with a polymer according to the invention. This will be referred to in Example 26.

The result is shown in FIG. 8. The grey bars correspond to peptide 1 and the white bars to peptide 2. Cn corresponds to the different concentrations of PsAcArF1 (1.1; 0.75; 0.03) and C'n corresponds to the different concentrations of PsAcAr1 (1.1; 0.75) with $1=10^{-6}$ M; $2=5 \times 10^{-7}$ M; $3=2.5 \times 10^{-7}$ M; $4=1.25 \times 10^{-7}$ M; $5=6.25 \times 10^{-8}$ M.

The intensity of the signals (on the y axis) that are associated with the wells treated with PsAcArF1 (1.1; 0.75; 0.03) and then incubated with the aldehyde peptide 1 is high (Cn, peptide 1). In comparison, the intensity of the signals associated with the wells treated with PsAcAr1 (1.1; 0.75) (control wells not having the hydrazide function that is reactive with respect to the aldehyde function of peptide 1) is very low (C'n, peptide 1).

In all cases, the intensity of the signals associated with the wells incubated with the control peptide 2 not having the aldehyde function is very low (Cn or C'n, peptide 2).

This example demonstrates chemoselective binding of the aldehyde peptide 1 to the wells treated with PsAcArF1 (1.1; 0.75; 0.03) and having accessible hydrazide functions.

Complementary experiments were carried out by varying the pH of the ligation reaction. The preferred pH for the reaction is 5, as expected for this type of chemical reaction.

Example 27

Functionalization of 96-Well Polystyrene Plates, Preparation of Biochips by Printing of Peptides and Reaction In Situ In this experiment, the wells are functionalized with a polysaccharide polymer. Peptides are printed to form a biochip, the peptides binding to the surface by formation of a hydrazone covalent bond.

The synthesis of the peptides used in this experiment is described in: Carion et al., Chemical Micropatterning of Polycarbonate for Site-Specific Peptide Immobilization and Biomolecular Interactions. *Chembiochem* 8, 315-322 (2007).

The peptides used are:

Ser-HA:
(SEQ ID NO: 3)
H-SGYPYDVPDYAGYPYDVPDYAGYPYDVPDYAS-NH$_2$;

Ser-FLAG:
(SEQ ID NO: 4)
H-SDYKDHDGDYKDHDIDYKDDDDKGGS-NH$_2$;

CHOCO-HA:
(SEQ ID NO: 5)
CHOCO-GYPYDVPDYAGYPYDVPDYAGYPYDVPDYAS-NH$_2$;

CHOCO-FLAG:
(SEQ ID NO: 6)
CHOCO-DYKDHDGDYKDHDIDYKDDDDKGGS-NH$_2$.

Protocol:

Printing of the peptides Ser-HA, CHOCO-HA, Ser-FLAG and CHOCO-FLAG, at a concentration of $10^4$ M in PBS buffer or acetate buffer at pH 5.5, on plates of the 96-well type, functionalized with polymer PsAcArF1 (10 µg/mL), polymer PsAcAr1 (10 µg/mL), PBS buffer or untreated.

Saturation of the wells is carried out with 300 µL of PBS+1% BSA for 30 min under stirring.

The wells are washed manually with PBS/0.1% Tween 20.

Incubation of anti-HA and anti-FLAG antibodies is carried out at a concentration of 1 µg/mL in PBS/0.1% BSA for 1.5 h under stirring (100 µL/well). The wells are washed manually with PBS/0.1% Tween 20.

Incubation of tetramethylrhodamine-labelled anti-IgG murine antibodies is carried out at a concentration of 2 µg/mL in PBS/0.1% BSA for 1 h under stirring (100 µL/well).

The wells are washed manually with PBS/0.1% Tween 20, 3 times with water, and dried by centrifugation (2500 r.p.m., 5 min, 20° C.).

The plates are read with a Técan scanner (focus offset: −1000/MTP gain: 90/resolution: 4 µm).

Figure 9:
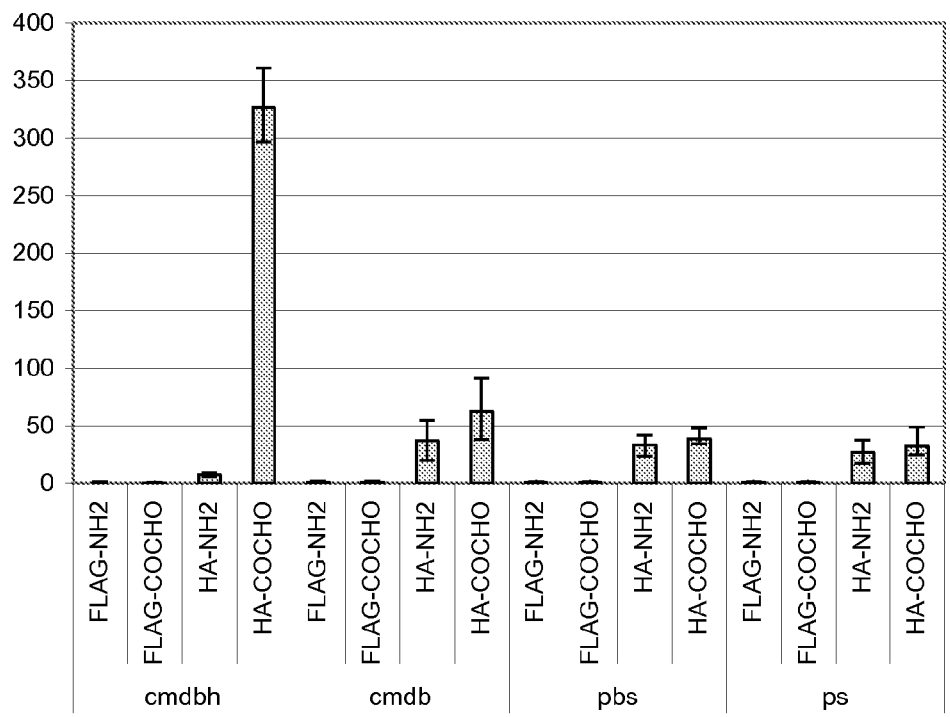
FIGS. 9 and 10 are histograms showing the functionalization of surfaces with peptides and detection with suitable antibodies (incubation with an anti-HA or anti-FLAG antibody). This will be referred to in Example 27.
Figure 10:
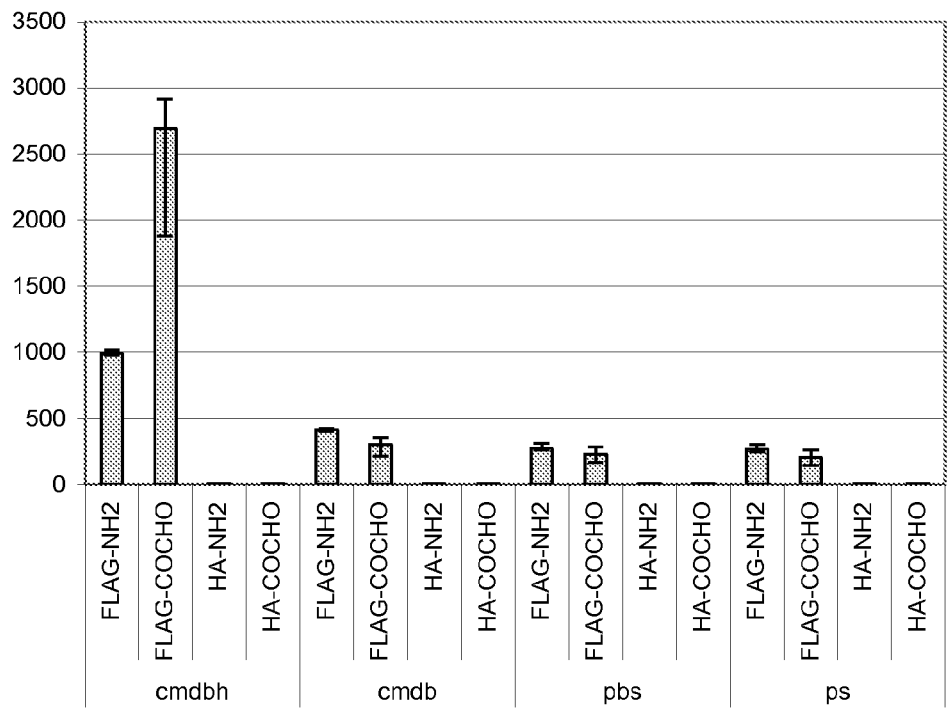

The results of incubation with the anti-HA antibody are shown in FIG. 9 and the results of incubation with the anti-FLAG antibody are shown in FIG. 10 (intensity of fluorescence on the y axis).

Example 28

Preparation of bis({2-[triphenylmethyl)sulphanyl]ethyl})amine 1.50 g of bis(2-chloroethyl)amine (8.4 mmol) and 4.65 g of triphenylmethanethiol (2 equivalents, 16.80 mmol) are introduced into a flask and placed under an inert atmosphere. 25 mL of anhydrous dimethylformamide (DMF) is added under magnetic stirring and the reaction mixture is cooled in an ice bath. 4 equivalents of 1,8-diazabicyclo[5,4,0]undec-7-ene (DBU) are added dropwise to the mixture. The mixture is stirred at ambient temperature for 3 hours and the reaction is monitored by thin-layer chromatography (TLC) (eluent: cyclohexane/ethyl acetate/triethylamine: 8/2/0.1). After this time, the solvent is evaporated off in a rotary evaporator. The white solid obtained is then dissolved in 50 mL of dichloromethane (DCM) and the product is extracted three times with a 5% aqueous solution of KH$_2$PO$_4$. The product is then purified by silica gel column chromatography (eluent: cyclohexane/EtOAc/triethylamine (TEA): 8/2/0.1), in order to obtain 1.46 g of amorphous white solid (yield of 28%).

The analysis of the product is as follows.
Rf=0.37 (silica gel, cyclohexane/EtOAc/TEA: 8/2/0.1).
$^1$H NMR (300 MHz, CDCl$_3$) δ 7.41-7.37 (m, 12H, Trt), 7.15-7.29 (m, 18H, Trt), 2.23-2.36 (m, 8H, CH$_2$), 1.26 (s, 1H, NH).
$^{13}$C (75 MHz, CDCl$_3$) 154.1; 129.8; 128.1; 126.9; 47.9; 32.6; MALDI-TOF: 243.1 [Trt$^+$], 622.3 [M+H$^+$]$^+$, 644.3 [M$^+$+Na$^+$].

Example 29

Synthesis of Boc-βAla-N(CH$_2$CH$_2$STrt)$_2$

Boc-β alanine (1.908 g, 10.1 mmol) is dissolved in 50 ml of dichloromethane, then the solution is cooled to 0° C. and N,N-dicyclohexyl-carbodiimide (5 mmol) is added. Stirring is maintained for 30 minutes at ambient temperature. After filtration, bis({2-(triphenylmethyl)sulphanyl]ethyl})amine (2.5 g, 4 mmol) is added. The reaction mixture is stirred for 2 hours at ambient temperature. The reaction mixture is evaporated to dryness. 100 mL of an aqueous soda solution (1 N) is added to the residue obtained, and it is extracted with dichloromethane (3×100 mL). The organic phase is dried over anhydrous magnesium sulphate, and evaporated. The crude product is purified by silica gel chromatography (cyclohexane/ethyl acetate/triethylamine, 80/20/0.1, v/v/v). The product Boc-βAla-N(CH$_2$CH$_2$STrt)$_2$ is obtained in the form of a white powder (3.1 g, 3.9 mmol, 97%).

The reaction diagram is as follows:

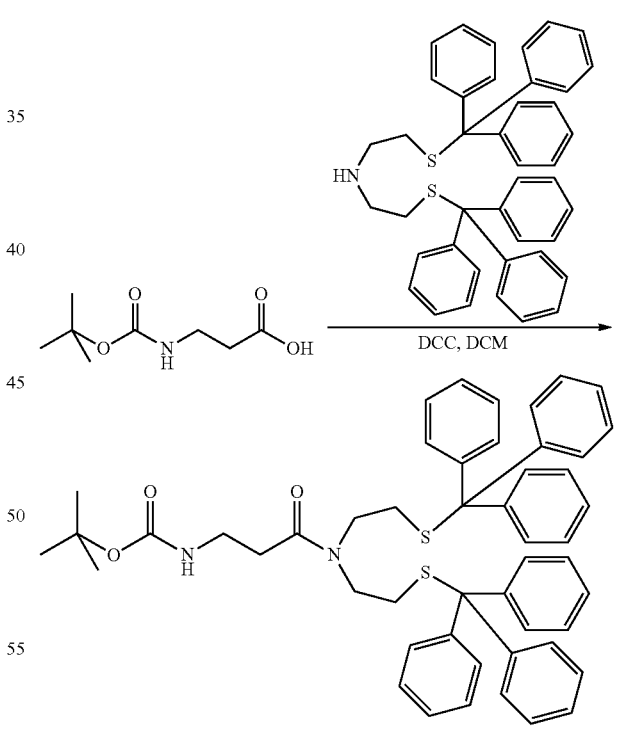

Melting point: 53° C.
$^1$H NMR (300 MHz, CDCl$_3$): δ ppm 1.43 (9H, s, CH$_3$); 1.94 (2H, t, J=4 Hz, CH$_2$S); 2.14 (2H, t, J=4 Hz, CH$_2$S); 2.31 (2H, t, J=4 Hz, CH$_2$CON); 2.73 (4H, m, CONCH$_2$); 3.23 (2H, m, OCONCH$_2$); 5.23 (H, m, CONH); 7.10-7.50 (30H$_{Ar}$, m).
$^{13}$C NMR (75 MHz, CDCl$_3$): δ ppm 28.50 (CH$_3$); 29.50 (CH$_2$); 30.0 (CH$_2$); 33.0 (CH$_2$); 36.0 (CH$_2$); 45.0 (CH$_2$);

47.0 (CH$_2$); 126.7 (CH); 127.0 (CH); 128.0 (CH); 129.5 (CH); 130.0 (CH); 143.0 (Cquat); 144.5 (Cquat); 145.0 (Cquat); 156.0 (Cquat); 171.0 (Cquat).

MALDI-TOF (DNB matrix): Mcalc=792.3 (C$_{50}$H$_{52}$N$_2$O$_3$S$_2$); m/z=815.4 [M+Na]; m/z=831.3 [M+K]$^+$.

Example 30

Synthesis of Boc-βAla-dithiazepane

The product Boc-βAla-dithiazepane (3 g, 3.78 mmol) is dissolved in dichloromethane (50 ml), and iodine (2.87 g, 11.3 mmol) is added. Stirring is maintained for 30 minutes at ambient temperature. The excess iodine is neutralized with an aqueous solution of sodium thiosulphate (3 M, 100 ml). Extraction is carried out with dichloromethane (4×100 mL). The organic phase is dried over anhydrous magnesium sulphate, and evaporated. The crude product is purified by silica gel chromatography (hexane/ethyl acetate/triethylamine, 40/60/0.1, v/v/v). The product Boc-βAla-dithiazepane is obtained in the form of a white paste (1.1 g, 3.6 mmol, 95%).

The reaction diagram is as follows:

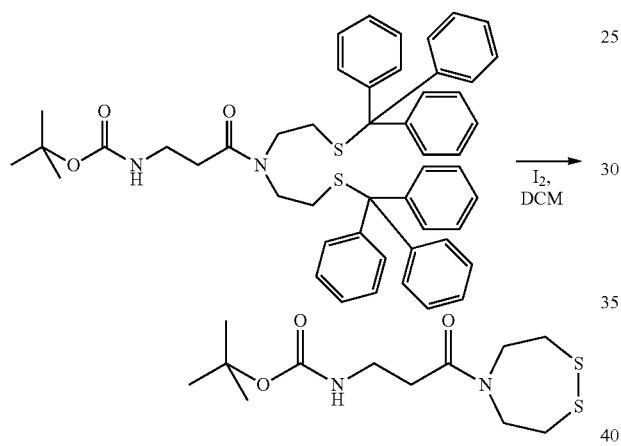

$^1$H NMR (300 MHz, CDCl$_3$): δ ppm 1.39 (9H, s, CH$_3$); 2.48 (2H, t, J=4 Hz, CH$_2$CON); 2.87 (2H, t, J=4 Hz, CH$_2$S); 3.04 (2H, t, J=4 Hz, CH$_2$S); 3.39 (2H, m, OCONCH$_2$); 3.76 (2H, t, J=4 Hz, CONCH$_2$); 3.86 (2H, t, J=4 Hz, CONCH$_2$); 5.25 (H, m, NH).

$^{13}$C NMR (75 MHz, CDCl$_3$): δ ppm 28.5 (CH$_3$); 33.0 (CH$_2$); 36.0 (CH$_2$); 37.0 (CH$_2$); 39.5 (CH$_2$); 50.0 (CH$_2$); 53.0 (CH$_2$); 143.0 (Cquat); 156.0 (Cquat); 172.0 (Cquat).

MALDI-TOF (DHB matrix): Mcalc=306.1 (C$_{12}$H$_{22}$N$_2$OS$_2$); m/z=307.1 [M+H]$^+$; m/z=329.1 [M+Na]$^+$; m/z=345.1 [M+K]$^+$.

Example 31

Synthesis of βAla-dithiazepane

The product Boc-βAla-dithiazepane (1 g, 3.26 mmol) is dissolved in dichloromethane (5 ml), and trifluoroacetic acid (5 mL) is added. Stirring is maintained for 30 minutes at ambient temperature. The reaction mixture is evaporated to dryness. Aqueous soda solution (1 N) is added to the residue obtained, and it is extracted with dichloromethane (3×100 mL). The organic phase is dried over anhydrous magnesium sulphate, and evaporated. The product NH$_2$-βAla-dithiazepane is obtained in the form of a translucent oil (628 mg, 3.04 mmol, 94%).

The reaction diagram is as follows:

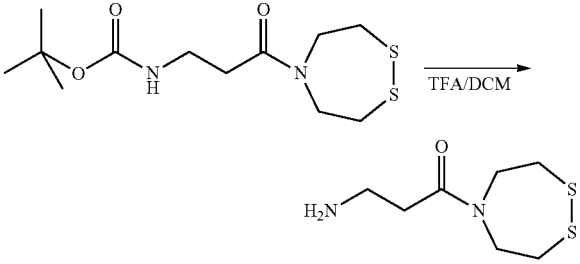

$^1$H NMR (300 MHz, CDCl$_3$): δ ppm 2.44 (2H, t, J=4 Hz, CH$_2$CON); 2.60 (H, m, NH$_2$); 2.90 (2H, t, J=4 Hz, NH$_2$CH$_2$); 3.0 (4H, m, CH$_2$S); 3.77 (2H, t, J=4 Hz, CONCH$_2$); 3.84 (2H, t, J=4 Hz, CONCH$_2$).

$^{13}$C NMR (75 MHz, CDCl$_3$): δ ppm 35.0 (CH$_2$); 35.5 (CH$_2$); 37.5 (CH$_2$); 39.0 (CH$_2$); 50.0 (CH$_2$); 52.0 (CH$_2$); 172.0 (Cquat).

MALDI-TOF (DHB matrix): Mcalc=206.05 (C$_7$H$_{14}$N$_2$OS$_2$); m/z=207.0 [M+H]$^+$; m/z=229.0 [M+Na]$^+$.

Example 32

Synthesis of the Polymer PsAcArF5

50 mg of polymer PsAcAr1 (1.1; 0.49) (0.20 mmol) is dissolved in 1 mL of deionized water in a flask, then the pH is adjusted to 4.74 with a 1N HCl solution. 1-cyclohexyl-3-(2-morpholino-ethyl)carbodiimide (CMC) (100 mg, 0.22 mmol, 1.1 eq) is added, then the pH is adjusted to 4.74. The amine H$_2$N(CH$_2$)$_2$CON(CH$_2$CH$_2$S—)$_2$ (75 mg, 0.36 mmol, 1.8 eq) is added. The reaction mixture is stirred overnight at ambient temperature.

The reaction mixture is then put in dialysis tubing (3500 g/mol; 1 mL/cm), then immersed in 2.5 L of a 2M NaCl solution, remaining there for 5 days, then in 2.5 L of water, where it also remains for 5 days.

The contents of the bag are then put in a pot, to be lyophilized to give 47 mg of PsAcArF5. The reaction diagram is as follows:

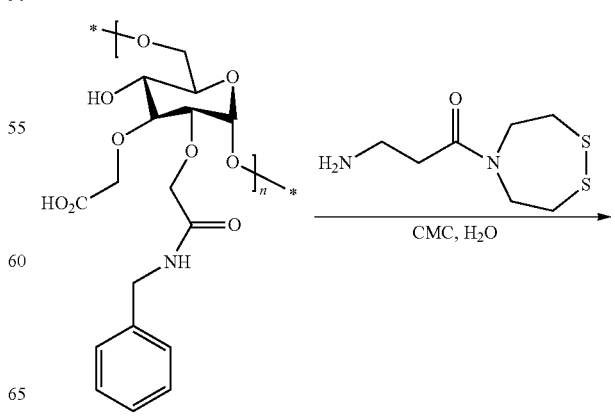

-continued

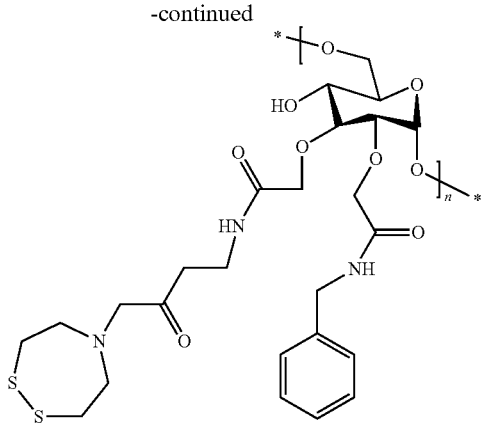

Example 33

Chemical Functionalization of 96-Well Polystyrene Plates, Amide Ligation with Fluorescent Peptides The polymers PsAcAr1 and PsAcArF5 were used in this example.

The polymer PsAcArF5 makes it possible to functionalize the bottom of the wells with a $CON(CH_2CH_2S—)_2$ function. The polymer PsAcAr1, which does not bear this function, serves as control. The $CON(CH_2CH_2S—)_2$ function can react with the molecules bearing a beta-aminothiol function, such as for example a cysteine present in the N-terminal position of peptides. The bond formed is an amide bond.

The chemistry of immobilization by the polymer PsAcArF5 is described in the following diagram:

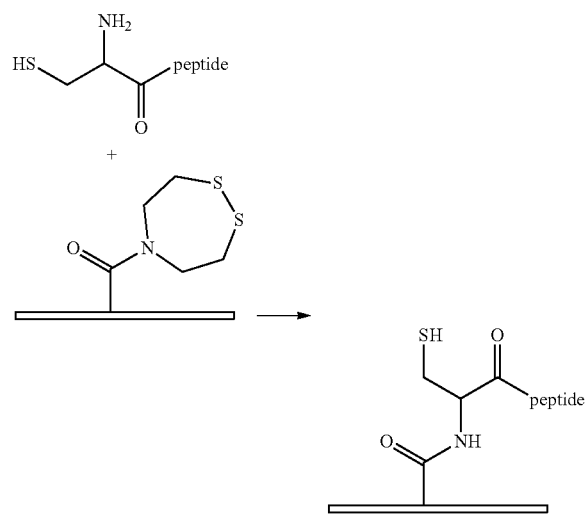

Two peptides are used in the present example:
1) H-CILK(rhodamine)EPVHGV-NH$_2$ (SEQ ID NO: 7);
2) H-SILK(rhodamine)EPVHGV-NH$_2$ (SEQ ID NO: 8).

These two peptides are synthesized according to the following protocol:

The peptide H-ILK(Mtt)E(tBu)PVH(Trt)GV-NH$_2$ (SEQ ID NO: 9) is assembled on a Novasyn TGR® resin (Novabiochem, 0.25 mmol, 0.23 mmol/g) using the Microwave Peptide Synthesizer (CEM) and the Fmoc/tert-butyl strategy. The deprotection of the Mtt group is carried out with a 1% TFA solution in $CH_2Cl_2$ (17×15 ml). The resin is neutralized with a 5% DIEA solution in $CH_2Cl_2$ (5×2 min) and then washed with $CH_2Cl_2$ (3×2 min), then with DMF (3×2 min). The resin is then reacted for 2 h with 5(6)-carboxytetramethylrhodamine (150.6 mg, 0.35 mmol), HOBT (47 mg, 0.35 mmol), HBTU (132.7 mg, 0.35 mmol) and DIEA (217.8 µl, 1.75 mmol, 5 eq) in DMF. The resin is then washed with DMF (4×2 min). The Fmoc terminal group is deprotected with a 20% solution of piperidine in DMF (5 and 15 min). The resin is washed with DMF (4×2 min). The resin is divided into two portions and is reacted with Fmoc-Cys (Trt)-OH or Fmoc-Ser(tBu)-OH respectively. Coupling is carried out manually using 4 equivalents of protected amino acid, 4 equivalents of HBTU and HOBT and 12 equivalents of DIEA. The resin is washed with DMF (4×2 min). The Fmoc terminal group is deprotected with a 20% solution of piperidine in DMF (5 and 15 min). The resin is then washed with DMF (4×2 min), $CH_2Cl_2$ (6×2 min), ethyl ether and then dried under reduced pressure. The deprotection and cleavage of the peptides are then carried out with a solution of TFA/$H_2$O/EDT/TIS: 94/2.5/2.5/1 by volume for peptide 1) and TFA/$H_2$OTIS: 95/2.5/2.5 by volume for peptide 2) for 1 h. The peptides are then precipitated from $Et_2$O/n-heptane solution: 1/1 by volume, solubilized in water and lyophilized. Purification is carried out by RP-HPLC and 41 mg (20%) and 28 mg (14%) are obtained for peptides 1) and 2) respectively.

MALDI-TOF (DHB matrix) Peptide 1): Mcalc=1505.7 ($C_{74}H_{104}N_{16}O_{16}S$); m/z=1506.8 [M+H]$^+$; m/z=1528.8 [M+Na]$^+$.

MALDI-TOF (DHB matrix) Peptide 2): Mcalc=1488.7 ($C_{75}H_{105}N_{15}O_{17}$); m/z=1489.7 [M+H]$^+$; m/z=1511.7 [M+Na]$^+$.

The polymers PsAcAr1 and PsAcArF5 are incubated in a 96-well polystyrene plate at a concentration of 10 µg/mL in PBS overnight at ambient temperature under stirring (100 µL/well).

The wells are then washed 6 times with a solution of PBS/0.1% Tween 20. The plate is dried in the centrifuge.

The peptides 1) and 2) are solubilized at a concentration of $10^{-4}$ M in 200 mM phosphate buffer in the presence of 200 mM of mercaptophenylacetic acid (MPAA), and 80 mM of tris(carboxyethyl)phosphine, at pH 7.6. These solutions are incubated for 10 min with stirring at 37° C. (60 µL/well) in the functionalized wells. The wells are then washed 6 times with a solution of PBS/0.1% Tween 20 and 3 times with deionized water. The plate is dried in the centrifuge (2500 r.p.m., 5 min, 20° C.). The plate is analysed in a Tecan fluorescence scanner.

Figure 11:
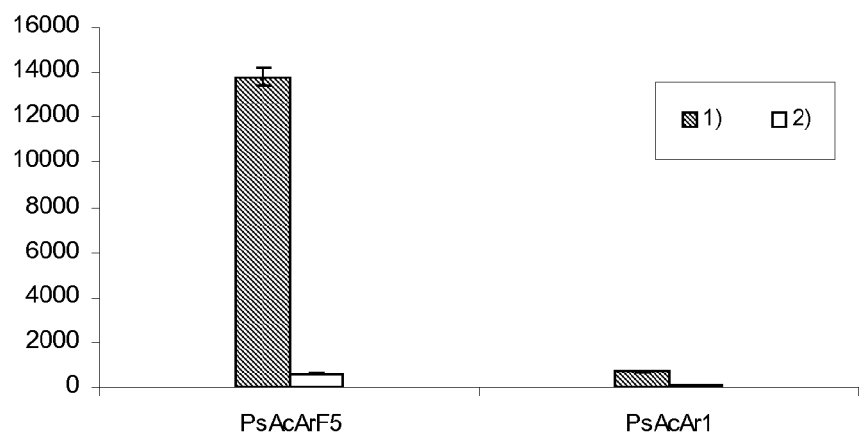
FIG. 11 is a histogram illustrating the chemoselective binding of a peptide bearing an N-terminal cysteine to a surface functionalized with a polymer according to the invention. This will be referred to in Example 33.

The results are shown in FIG. 11 (intensity of fluorescence on the y axis). This example demonstrates that the wells of the polystyrene plate functionalized by means of the polymer PsAcArF5 allow binding of the cysteine peptide 1) and not of the control serine peptide 2). The very weak signal obtained with the control polymer PsAcAr1 for the two peptides shows the importance of having a 2,5-dithiazepane function on the polystyrene surface for binding of the cysteine peptide 1).

Example 34

Preparation of a Biochip with Antibodies at the Bottom of 96-Well Polystyrene Plates In this example, the wells are functionalized by means of a polysaccharide, then the antibodies are printed to form a biochip. These proteins bind to the surface by the formation of non-covalent bonds. The biochips are then incubated with the target proteins.

8 wells of a 96-well polystyrene microplate (Maxisorp, Nunc-Immuno Plate) are treated with 100 µL of PsAcArF1 (1.15; 0.64; 0.26) at a concentration of 10 µg/mL in a buffer (conditions A). 8 wells are treated with the buffer only (conditions B). The treatment is carried out at ambient temperature overnight, under stirring.

The plate is then washed with the buffer using a plate washer (200 µL/well, 3 washings, stirring) then with deionized water using a plate washer (200 µL/well, 3 washings, stirring).

The anti-streptavidin antibody (rabbit anti-streptavidin polyclonal antibody, Antibodies-on line, reference ABIN107091) is then printed at the bottom of the wells solubilized in the buffer (3 spots per well, 8 wells for a total of 24 spots).

Saturation of the wells is carried out with 200 µL of buffer with 2% of BSA for 2 h.

The wells are washed with the automatic washer (3 cycles, stirring) with buffer with the addition of 0.05% of Tween 20.

Then the streptavidin-HRP (Streptavidin-HRP, reference Thermo-Pierce 21130) is incubated with a 1:10 000 dilution in buffer with the addition of Tween 20 at 0.05% and BSA at 0.2% for 1 h (100 µL/well). A supplementary experiment is carried out with a control protein: goat anti-mouse IgG HRP conjugate, Southern Biotech, ref 103105, diluted 1:6000 in the same solution.

The wells are washed with the automatic washer (3 cycles) with buffer containing 0.05% of Tween 20. Then it is incubated with an insoluble solution of TMB (3,3',5,5"-tetramethylbenzidine) for 12 minutes at ambient temperature. The wells are washed with 200 µL of deionized water.

An image of the bottom of each well is obtained using a CCD camera (resolution: 3 µm), which makes it possible to generate grey-scale images. The spots are then quantified by means of standard software for the quantification of microarrays.

Figure 12:
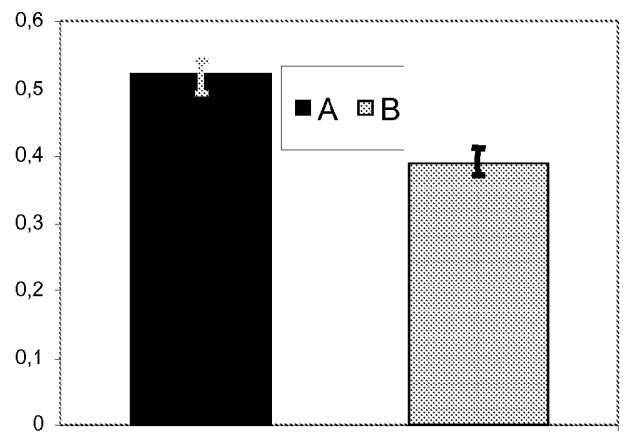
FIGS. 12 and 13 are diagrams illustrating colorimetric detection on an antibody biochip at the bottom of 96-well polystyrene plates. This will be referred to in Example 34.

The results of the intensities for all of the spots after incubation with streptavidin-HRP are shown in FIG. 12 (intensity in arbitrary units on the y axis; A: wells treated with PsAcArF1 (1.15; 0.64; 0.26); B: untreated control wells). Incubation with the control protein goat anti-mouse IgG HRP conjugate did not give any detectable signal.

This figure shows that the median intensity obtained for the spots of anti-streptavidin antibody within wells A is significantly higher than that of wells B.

Figure 13:
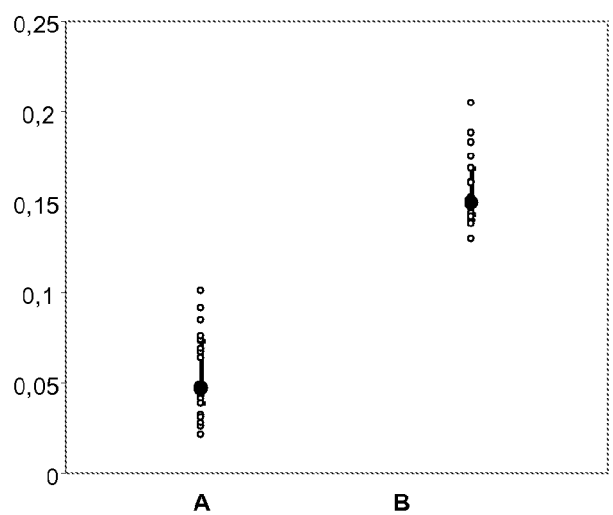

The results for the standard deviation of the pixels for each spot (empty circles), with the median and the interquartile deviation for all of the spots, are shown in FIG. 13. This standard deviation within the spots, which characterizes the quality of spotting, is very much lower for condition A compared with condition B.

Overall, these results show the superiority of treatment A for preparing biochips.

The invention claimed is:

1. Device for detecting analytes, comprising a plastic substrate at least partly covered directly with bonding polymers fixed to the substrate non-covalently, said bonding polymers comprising a polysaccharide skeleton provided with:
   aromatic groups of the form —X—CONH—Z, where X represents a linear or branched, substituted or unsubstituted alkyl chain, comprising 1 to 6 carbon atoms, and Z represents an aryl function;
   carboxylic acid groups of the form —X—COOH, where X represents a linear or branched, substituted or unsubstituted alkyl chain, comprising 1 to 6 carbon atoms; and
   reactive F groups selected from:
      groups of the form —X—CONH—X'—N$_3$;
      groups of the form —X—CONH—NH$_2$;
      groups of formula (V):

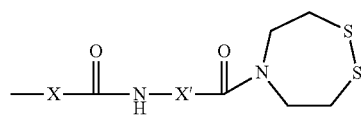

groups of formula (V'):

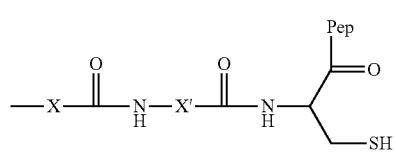

where X and X' each represent a substituted or unsubstituted alkyl chain comprising from 1 to 6 carbon atoms and Pep represents a peptide fragment.

2. Device according to claim 1, in which the polysaccharide skeleton is a dextran skeleton.

3. Device according to claim 1, in which:
   X is CH$_2$; and/or
   Z is —CH$_2$-Ph or —CH$_2$-Ph-paraOH.

4. Device according to claim 1, in which the bonding polymers comprise:
   from 0.4 to 0.8 aromatic groups per saccharide unit of the polysaccharide skeleton; and/or
   from 0 to 0.8 reactive F groups, per saccharide unit of the polysaccharide skeleton; and/or
   from 0.5 to 1.5 aromatic, carboxylic acid and reactive F groups in total, per saccharide unit of the polysaccharide skeleton.

5. Device according to claim 1, in which the substrate is a substrate of polystyrene, polycarbonate, poly(methyl methacrylate) or polypropylene.

6. Device according to claim 1, comprising capturing elements immobilized on the bonding polymers.

7. Device according to claim 6, in which the capturing elements are selected from:
   polypeptides;
   saccharides, oligosaccharides and lipopolysaccharides;
   viruses or virus fragments and cells.

8. Device according to claim 1, comprising a plurality of detection zones.

9. Device according to claim 1, in which the substrate is an opaque or transparent slide, a microtitre plate, a collection of beads, a culture plate, a strip or a stick.

10. Method of detecting chemical molecules, biological molecules, cells or living organisms comprising a step of contacting said chemical molecules, biological molecules, cells or living organisms with the device for detecting analytes according to claim 1.

11. Bonding polymer that can be used in the device according to claim 1 comprising a polysaccharide skeleton provided with:
   0.4 to 0.8 aromatic groups per saccharide unit of the form —X—CONH—Z, where X represents a linear or branched, substituted or unsubstituted alkyl chain, comprising 1 to 6 carbon atoms, and Z represents an aryl function;
   carboxylic acid groups of the form —X—COOH, where X represents a linear or branched alkyl chain, comprising 1 to 6 carbon atoms; and
   reactive F groups selected from:
      groups of the form —X—CONH—X'—N$_3$;
      groups of the form —X—CONH—NH$_2$;
      groups of formula (V):

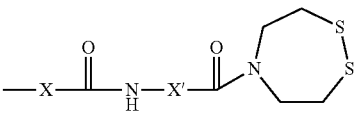

groups of formula (V'):

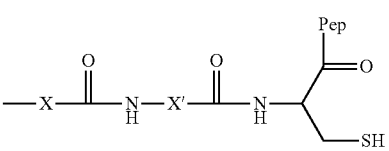

where X and X' each represent a substituted or unsubstituted alkyl chain comprising from 1 to 6 carbon atoms and Pep represents a peptide fragment.

12. Bonding polymer according to claim 11, in which the polysaccharide skeleton is a dextran skeleton.

13. Bonding polymer according to claim 11, in which:
X and/or X' is $CH_2$; and/or
X and/or X' is $(CH_2)_2$; and/or
Z is —$CH_2$-Ph or —$CH_2$-Ph-paraOH.

14. Bonding polymer according to claim 11, comprising:
from 0.4 to 0.6 aromatic groups per saccharide unit of the polysaccharide skeleton; and/or
from 0 to 0.8 reactive F groups per saccharide unit of the polysaccharide skeleton; and/or
from 0.5 to 1.5 aromatic, carboxylic acid and reactive F groups in total, per saccharide unit of the polysaccharide skeleton.

* * * * *